United States Patent
Puckett et al.

(10) Patent No.: US 10,010,395 B2
(45) Date of Patent: *Jul. 3, 2018

(54) COMPOSITE PROSTHETIC DEVICES

(71) Applicant: Zeus Industrial Products, Inc., Orangeburg, SC (US)

(72) Inventors: Sabrina D. Puckett, Lexington, SC (US); Joshua Manasco, West Columbia, SC (US); Robert L. Ballard, Orangeburg, SC (US); Bruce L. Anneaux, Lexington, SC (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/520,368

(22) Filed: Oct. 22, 2014

(65) Prior Publication Data

US 2016/0081783 A1 Mar. 24, 2016

Related U.S. Application Data

(63) Continuation of application No. 13/803,892, filed on Mar. 14, 2013, now abandoned.
(Continued)

(51) Int. Cl.
*A61F 2/00* (2006.01)
*A61F 2/06* (2013.01)
(Continued)

(52) U.S. Cl.
CPC .............. *A61F 2/0077* (2013.01); *A61F 2/06* (2013.01); *A61F 2/07* (2013.01); *A61F 2/86* (2013.01);
(Continued)

(58) Field of Classification Search
CPC .. A61F 2/0077; A61F 2/07; A61F 2/86; A61F 2/06; A61F 2002/072;
(Continued)

(56) References Cited

U.S. PATENT DOCUMENTS 2,158,416 A    5/1939   Formhals
4,043,331 A    8/1977   Martin et al.
(Continued)

FOREIGN PATENT DOCUMENTS

CN    101003917 A    7/2007
CN    101350413      1/2009
(Continued)

OTHER PUBLICATIONS

U.S. Office Action dated Oct. 10, 2014, from U.S. Appl. No. 13/742,025, filed Jan. 15, 2013.
(Continued)

*Primary Examiner* — Christopher D Prone
*Assistant Examiner* — Rokhaya Diop
(74) *Attorney, Agent, or Firm* — Louis Isaf; Womble Bond Dickinson (US) LLP

(57) ABSTRACT

The present disclosure provides composite prosthetic devices including two or more layers of electrospun polymers and methods of preparation thereof. In some embodiments, the two or more layers can be porous and in other embodiments, one or more components is nonporous. The composite prosthetic devices can include various materials and the properties of the prosthetic devices can be tailored for use in a range of different applications.

19 Claims, 11 Drawing Sheets

Related U.S. Application Data

(60) Provisional application No. 61/620,633, filed on Apr. 5, 2012, provisional application No. 61/724,731, filed on Nov. 9, 2012.

(51) Int. Cl.

| | | |
|---|---|---|
| *A61F 2/86* | (2013.01) | |
| *A61L 31/10* | (2006.01) | |
| *A61L 31/14* | (2006.01) | |
| *D01D 5/00* | (2006.01) | |
| *D01D 10/02* | (2006.01) | |
| *D01F 6/12* | (2006.01) | |
| *D04H 1/728* | (2012.01) | |
| *A61F 2/07* | (2013.01) | |

(52) U.S. Cl.
CPC ............. *A61L 31/10* (2013.01); *A61L 31/146* (2013.01); *D01D 5/003* (2013.01); *D01D 10/02* (2013.01); *D01F 6/12* (2013.01); *D04H 1/728* (2013.01); *A61F 2002/0086* (2013.01); *A61F 2002/072* (2013.01); *A61L 2400/12* (2013.01); *A61L 2420/08* (2013.01); *D10B 2321/042* (2013.01); *D10B 2509/06* (2013.01)

(58) Field of Classification Search
CPC . A61F 2002/0086; D04H 1/728; A61L 31/10; A61L 31/146; A61L 2420/08; A61L 2400/12; D01F 6/12; D01D 5/003; D01D 10/02; D10B 2509/06; D10B 2321/042
See application file for complete search history.

(56) References Cited

U.S. PATENT DOCUMENTS

| | | |
|---|---|---|
| 4,044,404 A | 8/1977 | Martin et al. |
| 4,096,227 A | 6/1978 | Gore |
| 4,127,706 A | 11/1978 | Martin et al. |
| 4,143,196 A | 3/1979 | Simm et al. |
| 4,287,139 A | 9/1981 | Guignard |
| 4,323,525 A | 4/1982 | Bornat |
| 4,432,916 A | 2/1984 | Logan |
| 4,552,707 A | 11/1985 | How |
| 4,689,186 A | 8/1987 | Bornat |
| 5,234,739 A | 8/1993 | Tanaru et al. |
| 5,324,785 A | 6/1994 | Noda et al. |
| 5,328,946 A | 7/1994 | Tuminello et al. |
| 5,344,297 A | 9/1994 | Hills |
| 5,476,589 A | 12/1995 | Bacino |
| 5,507,770 A | 4/1996 | Turk |
| 5,509,902 A | 4/1996 | Raulerson |
| 5,562,986 A | 10/1996 | Yamamoto et al. |
| 5,665,428 A | 9/1997 | Cha et al. |
| 5,700,572 A | 12/1997 | Klatt et al. |
| 5,702,658 A | 12/1997 | Pellegrin et al. |
| 5,741,333 A | 4/1998 | Frid |
| 5,806,633 A | 9/1998 | Macuga |
| 5,824,046 A | 10/1998 | Smith et al. |
| 5,874,165 A | 2/1999 | Drumheller |
| 5,912,077 A | 6/1999 | Tamaru et al. |
| 5,993,489 A | 11/1999 | Lewis et al. |
| 6,001,125 A | 12/1999 | Golds et al. |
| 6,075,180 A | 6/2000 | Sharber et al. |
| 6,124,523 A | 9/2000 | Banas et al. |
| 6,133,165 A | 10/2000 | Tamaru et al. |
| 6,175,571 B1 | 1/2001 | Haddock et al. |
| 6,214,039 B1 | 4/2001 | Banas et al. |
| 6,264,684 B1 | 7/2001 | Banas et al. |
| 6,265,333 B1 | 7/2001 | Dzenis et al. |
| 6,270,523 B1 | 8/2001 | Herweck et al. |
| 6,312,462 B1 | 11/2001 | McDermott et al. |
| 6,383,214 B1 | 5/2002 | Banas et al. |
| 6,402,779 B1 | 6/2002 | Colone et al. |
| 6,416,896 B1 | 7/2002 | Tamaru et al. |
| 6,436,135 B1 | 8/2002 | Goldfarb |
| 6,488,701 B1 | 12/2002 | Nolting et al. |
| 6,498,207 B1 | 12/2002 | Hoshikawa et al. |
| 6,505,654 B1 | 1/2003 | Andersen et al. |
| 6,524,334 B1 | 2/2003 | Thompson |
| 6,547,814 B2 | 4/2003 | Edwin et al. |
| 6,579,314 B1 | 6/2003 | Lombardi et al. |
| 6,592,614 B2 | 7/2003 | Lenker et al. |
| 6,641,773 B2 | 11/2003 | Kleinmeyer et al. |
| 6,673,105 B1 | 1/2004 | Chen |
| 6,679,913 B2 | 1/2004 | Homsy |
| 6,699,276 B2 | 3/2004 | Sogard et al. |
| 6,709,455 B1 | 3/2004 | Chouinard |
| 6,740,115 B2 | 5/2004 | Lombardi et al. |
| 6,743,273 B2 | 6/2004 | Chung et al. |
| 6,752,826 B2 | 6/2004 | Holloway et al. |
| 6,770,087 B2 | 8/2004 | Layne et al. |
| 6,790,225 B1 | 9/2004 | Shannon et al. |
| 6,797,217 B2 | 9/2004 | McCrea et al. |
| 6,808,533 B1 | 10/2004 | Goodwin et al. |
| 6,827,737 B2 | 12/2004 | Hill et al. |
| 6,833,153 B1 | 12/2004 | Roorda et al. |
| 6,863,852 B1 | 3/2005 | Ballard et al. |
| 6,899,727 B2 | 5/2005 | Armstrong et al. |
| 6,939,372 B2 | 9/2005 | Dong |
| 6,949,119 B2 | 9/2005 | Myers |
| 6,974,474 B2 | 12/2005 | Pavcnik et al. |
| 7,083,640 B2 | 8/2006 | Lombardi et al. |
| 7,083,697 B2 | 8/2006 | Dao et al. |
| 7,108,912 B2 | 9/2006 | Huang et al. |
| 7,115,220 B2 | 10/2006 | Dubson et al. |
| 7,118,592 B1 | 10/2006 | Dang et al. |
| 7,186,263 B2 | 3/2007 | Golds et al. |
| 7,220,276 B1 | 5/2007 | Williams et al. |
| 7,244,271 B2 | 7/2007 | Lentz et al. |
| 7,244,272 B2 | 7/2007 | Dubson et al. |
| 7,285,132 B2 | 10/2007 | Tseng et al. |
| 7,306,729 B2 | 12/2007 | Bacino et al. |
| 7,316,754 B2 | 1/2008 | Ide et al. |
| 7,354,449 B2 | 4/2008 | Goodwin et al. |
| 7,413,575 B2 | 8/2008 | Phaneuf et al. |
| 7,416,559 B2 | 8/2008 | Shalaby |
| 7,452,371 B2 | 11/2008 | Pavcnik et al. |
| 7,468,071 B2 | 12/2008 | Edwin et al. |
| 7,485,141 B2 | 2/2009 | Marercak et al. |
| 7,510,571 B2 | 3/2009 | Spiridigliozzi et al. |
| 7,520,894 B2 | 4/2009 | Pavcnik et al. |
| 7,524,527 B2 | 4/2009 | Stenzel |
| 7,550,004 B2 | 6/2009 | Bahler et al. |
| 7,560,006 B2 | 7/2009 | Rakos et al. |
| 7,582,240 B2 | 9/2009 | Marin et al. |
| 7,597,710 B2 | 10/2009 | Obermiller |
| 7,641,681 B2 | 1/2010 | Sherry et al. |
| 7,659,219 B2 | 2/2010 | Biran et al. |
| 7,691,141 B2 | 4/2010 | Lewis et al. |
| 7,727,271 B2 | 6/2010 | Kujawski et al. |
| 7,799,261 B2 | 9/2010 | Orr et al. |
| 7,857,608 B2 | 12/2010 | Fabbricante et al. |
| 7,872,073 B2 | 1/2011 | Jones |
| 7,922,761 B2 | 4/2011 | Shalev et al. |
| 7,947,069 B2 | 5/2011 | Sanders |
| 7,981,353 B2 | 7/2011 | Mitchell et al. |
| 8,178,030 B2 | 5/2012 | Anneaux et al. |
| 8,257,640 B2 | 9/2012 | Ballard et al. |
| 8,262,979 B2 | 9/2012 | Anneaux et al. |
| 8,637,144 B2 | 1/2014 | Ford |
| 8,658,707 B2 | 2/2014 | Xu et al. |
| 8,691,543 B2 | 4/2014 | Gaudette et al. |
| 8,771,582 B2 | 7/2014 | Phaneuf et al. |
| 2001/0026231 A1 | 2/2001 | Shannon et al. |
| 2001/0000188 A1 | 4/2001 | Lenker et al. |
| 2001/0010012 A1 | 7/2001 | Edwin et al. |
| 2001/0020181 A1 | 9/2001 | Layne |
| 2001/0021870 A1 | 9/2001 | Edwin et al. |
| 2001/0032008 A1 | 10/2001 | Wang et al. |
| 2001/0049551 A1 | 12/2001 | Tseng et al. |
| 2002/0045931 A1 | 4/2002 | Sogard et al. |
| 2002/0111667 A1 | 8/2002 | Girton et al. |
| 2002/0111668 A1 | 8/2002 | Smith |

(56) References Cited

U.S. PATENT DOCUMENTS

| | | |
|---|---|---|
| 2002/0178570 A1 | 12/2002 | Sogard et al. |
| 2002/0192468 A1 | 12/2002 | Choi |
| 2002/0198588 A1 | 12/2002 | Armstrong et al. |
| 2003/0004559 A1 | 1/2003 | Lentz et al. |
| 2003/0006528 A1 | 1/2003 | Edwin et al. |
| 2003/0008944 A1 | 1/2003 | Jones et al. |
| 2003/0040772 A1 | 2/2003 | Hyodoh et al. |
| 2003/0044559 A1 | 3/2003 | Liu et al. |
| 2003/0044585 A1 | 3/2003 | Taylor et al. |
| 2003/0060871 A1 | 3/2003 | Hill et al. |
| 2003/0069343 A1 | 4/2003 | Smith et al. |
| 2003/0074049 A1 | 4/2003 | Hoganson et al. |
| 2003/0100944 A1 | 5/2003 | Laksin et al. |
| 2003/0114917 A1 | 6/2003 | Holloway et al. |
| 2003/0152598 A1 | 8/2003 | Ashton et al. |
| 2003/0191522 A1 | 10/2003 | Myers |
| 2003/0195611 A1 | 10/2003 | Greenhalgh et al. |
| 2003/0204241 A1 | 10/2003 | Dong |
| 2003/0209835 A1 | 11/2003 | Chun et al. |
| 2003/0211135 A1 | 11/2003 | Greenhalgh et al. |
| 2004/0016260 A1 | 1/2004 | Kobayashi et al. |
| 2004/0030377 A1* | 2/2004 | Dubson .............. A61F 2/07 623/1.13 |
| 2004/0033364 A1 | 2/2004 | Spiridigliozzi et al. |
| 2004/0049264 A1 | 3/2004 | Sowinski et al. |
| 2004/0051201 A1 | 3/2004 | Greenhalgh et al. |
| 2004/0054397 A1 | 3/2004 | Smith et al. |
| 2004/0093070 A1 | 5/2004 | Hojeibanet al. |
| 2004/0110439 A1 | 6/2004 | Chaikof et al. |
| 2004/0167606 A1 | 8/2004 | Chouinard |
| 2004/0236402 A1 | 11/2004 | Layne et al. |
| 2005/0004653 A1 | 1/2005 | Gerberding et al. |
| 2005/0025974 A1 | 2/2005 | Lennhoff |
| 2005/0053782 A1 | 3/2005 | Sen et al. |
| 2005/0113868 A1 | 5/2005 | Devellian et al. |
| 2005/0113886 A1 | 5/2005 | Devellian |
| 2005/0113909 A1 | 5/2005 | Shannon et al. |
| 2005/0131519 A1 | 6/2005 | Hartley |
| 2005/0137675 A1 | 6/2005 | Dubson et al. |
| 2005/0143494 A1 | 6/2005 | Jones |
| 2005/0149170 A1* | 7/2005 | Tassel ............... A61B 5/0031 623/1.15 |
| 2005/0154448 A1 | 7/2005 | Cully et al. |
| 2005/0187605 A1 | 8/2005 | Greenhalgh et al. |
| 2005/0244453 A1 | 11/2005 | Stucke et al. |
| 2005/0278018 A1 | 12/2005 | Jensen |
| 2005/0283224 A1 | 12/2005 | King |
| 2005/0288767 A1 | 12/2005 | Kujawski et al. |
| 2006/0015171 A1 | 1/2006 | Armstrong |
| 2006/0020328 A1 | 1/2006 | Tan |
| 2006/0074482 A1 | 4/2006 | Lewis et al. |
| 2006/0200232 A1 | 9/2006 | Phaneuf et al. |
| 2006/0213829 A1 | 9/2006 | Rutledge et al. |
| 2006/0259133 A1 | 11/2006 | Sowinski et al. |
| 2006/0266474 A1 | 11/2006 | Burnside et al. |
| 2007/0026036 A1 | 2/2007 | Falotico et al. |
| 2007/0031607 A1 | 2/2007 | Dubson et al. |
| 2007/0043428 A1 | 2/2007 | Jennings et al. |
| 2007/0087027 A1 | 4/2007 | Greenhalgh et al. |
| 2007/0132130 A1 | 6/2007 | Roberts |
| 2007/0191936 A1 | 8/2007 | Williams et al. |
| 2007/0207179 A1 | 9/2007 | Andersen et al. |
| 2007/0207186 A1 | 9/2007 | Scanlon et al. |
| 2007/0208410 A1 | 9/2007 | Berra et al. |
| 2007/0244539 A1 | 10/2007 | Lentz et al. |
| 2007/0244569 A1 | 10/2007 | Weber et al. |
| 2007/0276477 A1 | 11/2007 | Lee et al. |
| 2008/0009781 A1 | 1/2008 | Anwar et al. |
| 2008/0021545 A1 | 1/2008 | Reneker et al. |
| 2008/0029617 A1 | 2/2008 | Marshall et al. |
| 2008/0033522 A1 | 2/2008 | Grewe et al. |
| 2008/0038976 A1 | 2/2008 | Berrigan et al. |
| 2008/0119943 A1 | 5/2008 | Armstrong et al. |
| 2008/0143012 A1 | 6/2008 | Norvell et al. |
| 2008/0161907 A1 | 7/2008 | Chen et al. |
| 2008/0167708 A1 | 7/2008 | Molland et al. |
| 2008/0199506 A1 | 8/2008 | Horres et al. |
| 2008/0208323 A1 | 8/2008 | El-Kurdi et al. |
| 2008/0208325 A1 | 8/2008 | Helmus et al. |
| 2008/0242171 A1 | 10/2008 | Huang et al. |
| 2008/0254091 A1 | 10/2008 | Lee et al. |
| 2008/0261043 A1 | 10/2008 | Greiner et al. |
| 2008/0264259 A1 | 10/2008 | Leung |
| 2008/0296808 A1 | 12/2008 | Joo et al. |
| 2008/0319530 A1 | 12/2008 | Leewood et al. |
| 2009/0012607 A1 | 1/2009 | Kim et al. |
| 2009/0018643 A1 | 1/2009 | Hashi et al. |
| 2009/0076587 A1 | 3/2009 | Cully et al. |
| 2009/0088828 A1 | 4/2009 | Shalev et al. |
| 2009/0125092 A1 | 5/2009 | McCrea et al. |
| 2009/0136651 A1 | 5/2009 | Larsen et al. |
| 2009/0157173 A1 | 6/2009 | Bjork et al. |
| 2009/0160099 A1 | 6/2009 | Huang |
| 2009/0163994 A1 | 6/2009 | Quigley et al. |
| 2009/0187240 A1 | 7/2009 | Clerc et al. |
| 2009/0192627 A1 | 7/2009 | Shin et al. |
| 2009/0227165 A1 | 9/2009 | Imai |
| 2009/0233057 A1 | 9/2009 | Aksay et al. |
| 2009/0248131 A1 | 10/2009 | Greenan |
| 2009/0258958 A1 | 10/2009 | Ford |
| 2009/0270907 A1 | 10/2009 | Todd et al. |
| 2009/0280325 A1 | 11/2009 | Lozano et al. |
| 2009/0312834 A1 | 12/2009 | Wood et al. |
| 2009/0324680 A1 | 12/2009 | Reneker |
| 2009/0324950 A1 | 12/2009 | Kim |
| 2010/0010515 A1 | 1/2010 | Farnsworth et al. |
| 2010/0013126 A1 | 1/2010 | Ishaque et al. |
| 2010/0074934 A1 | 3/2010 | Hunter |
| 2010/0093093 A1 | 4/2010 | Leong et al. |
| 2010/0107881 A1 | 5/2010 | Healey et al. |
| 2010/0190254 A1 | 7/2010 | Chian et al. |
| 2010/0194000 A1 | 8/2010 | Petras et al. |
| 2010/0248324 A1 | 9/2010 | Xu et al. |
| 2010/0304205 A1 | 12/2010 | Jo et al. |
| 2010/0331965 A1 | 12/2010 | Dugas et al. |
| 2011/0022159 A1 | 1/2011 | Fierens et al. |
| 2011/0030885 A1* | 2/2011 | Anneaux .............. A61L 31/06 156/187 |
| 2011/0031656 A1 | 2/2011 | Anneaux et al. |
| 2011/0089603 A1 | 4/2011 | Fabbricane et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2012/0114722 A1 | 5/2012 | Ballard et al. |
| 2012/0201988 A1 | 8/2012 | Hansen et al. |
| 2013/0085565 A1 | 4/2013 | Eller et al. |
| 2013/0184808 A1 | 7/2013 | Hall et al. |
| 2013/0184810 A1 | 7/2013 | Hall et al. |
| 2013/0189464 A1 | 7/2013 | Ford |
| 2014/0067047 A1 | 3/2014 | Eller et al. |
| 2014/0072694 A1 | 3/2014 | Hall et al. |
| 2014/0074225 A1 | 3/2014 | Hall et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0248418 A1 | 9/2014 | Eller et al. |
| 2014/0249619 A1 | 9/2014 | Eller et al. |
| 2014/0273703 A1 | 9/2014 | Mower et al. |

FOREIGN PATENT DOCUMENTS

| | | |
|---|---|---|
| CN | 101530750 A | 9/2009 |
| CN | 101994161 A | 3/2011 |
| CN | 103561682 A | 2/2014 |
| EP | 0 005 035 | 10/1979 |
| EP | 2 223 725 | 9/2010 |
| EP | 2363516 | 9/2011 |
| GB | 1 530 990 | 11/1978 |
| GB | 2015118 | 9/1979 |
| JP | 02-0571379 | 10/1996 |
| JP | 2006-326579 | 12/2006 |
| JP | 2007-224466 | 9/2007 |
| KR | 10-0820162 | 4/2008 |
| KR | 10-0845239 | 7/2008 |

(56) References Cited

FOREIGN PATENT DOCUMENTS

| KR | 10-2012-0116640 | 10/2012 |
| WO | WO 1998/031306 | 7/1998 |
| WO | WO 2005/018600 | 3/2005 |
| WO | WO 2005/060875 | 7/2005 |
| WO | WO 2005/095684 A1 | 10/2005 |
| WO | WO 2007/145283 | 12/2007 |
| WO | WO 2008/022993 | 2/2008 |
| WO | WO 2008/109116 | 9/2008 |
| WO | WO 2009/018463 | 2/2009 |
| WO | WO 2009/127170 | 10/2009 |
| WO | WO 2010/083530 | 7/2010 |
| WO | WO2010132636 | 11/2010 |
| WO | WO 2011/017698 | 2/2011 |
| WO | WO 2011/056154 | 5/2011 |
| WO | WO 2012/103501 | 8/2012 |
| WO | WO 2012/103501 A1 | 8/2012 |
| WO | WO 2012/122485 | 9/2012 |
| WO | WO 2013/109528 | 7/2013 |
| WO | WO 2014/007979 | 1/2014 |
| WO | WO 2014/047065 | 3/2014 |
| WO | WO 2014/047379 | 3/2014 |
| WO | WO 2014/159710 A1 | 10/2014 |

OTHER PUBLICATIONS

Role of chain entanglements on fiber formation during electrospinning of polymer solutions: good solvent, non-specific polymer-polymer interaction limit—Shenoy et al.—Science Direct (2005)—pp. 3372-3384.
Kim et al., "Structural Studies of Electrospun Cellulose Nanofibers," Polymer, 2006, pp. 5097-5107, vol. 47.
PCT International Search Report from PCT/US10/021426, dated Aug. 16, 2010.
Written Opinion of the International Searching Authority, PCT/US10/021426, dated Aug. 16, 2010.
International Search Report (PCT/US2010/044874)—2 pages.
International Search Report (PCT/US2010/044879)—2 pages.
PCT Written Opinion from International Application No. PCT/US2010/044874, filed Aug. 9, 2010 (8 pages).
PCT Written Opinion from International Application No. PCT/US2010/044879, filed Aug. 9, 2010 (6 pages).
International Search Report & Written Opinion dated Feb. 25, 2013, for PCT Application No. PCT/US12/056757, filed Sep. 21, 2012.
Office Action dated Sep. 22, 2014 from U.S. Appl. No. 13/787,327, filed Mar. 6, 2013.
Electrospinning of cyclodextrin functionalized polyethylene oxide (PEO) nanofibers; European Polymer Journal, Pergamon Press Ltd., Oxford, GB, vol. 45, No. 4, Dec. 25, 2008, pp. 1032-1037.
Supplementary Partial European Search Report from co-pending European patent application 10807285.1, dated Aug. 19, 2013.
Supplementary Partial European Search Report from co-pending European patent application 10807287.7, dated Aug. 19, 2013.
Office Action dated May 9, 2014 from U.S. Appl. No. 13/360,444, filed Jan. 27, 2012.
Response to May 9, 2014 Office Action filed Aug. 11, 2014 from U.S. Appl. No. 13/360,444, filed Jan. 27, 2012.
Office Action dated Jul. 2, 2014 from U.S. Appl. No. 14/044,050, filed Oct. 2, 2013.
Office Action dated Aug. 29, 2014 from U.S. Appl. No. 14/152,590, filed Jan. 10, 2014.
Office Action dated Mar. 3, 2014 from U.S. Appl. No. 13/742,025, filed Jan. 15, 2013.
Response to Mar. 3, 2014 Office Action filed Jun. 19, 2014 from U.S. Appl. No. 13/742,025, filed Jan. 15, 2013.
International Search Report and Written Opinion dated May 23, 2012 for PCT/US2012/023006.
Preparation of polytetrafluoroethylene ultrafine fiber mats with electrospinning process; Sijun et al.; Materials Science Forum vols. 675-677 (2011); pp. 827-830.
U.S. Appl. No. 13/787,327, filed Mar. 6, 2013, Hall et al.

U.S. Appl. No. 13/826,618, filed Mar. 14, 2013, Hall et al.
U.S. Appl. No. 13/827,775, filed Mar. 14, 2013, Lampropoulos et al.
U.S. Appl. No. 13/829,452, filed Mar. 14, 2013, Hall et al.
Final Office Action for U.S. Appl. No. 13/446,300, dated Dec. 2, 2016.
Office Action for EP application No. 13741191.4, dated Dec. 2, 2016.
RCE and Response to Final Office Action for U.S. Appl. No. 14/152,590, dated Dec. 21, 2016.
Final Office Action for U.S. Appl. No. 13/826,618, dated Nov. 18, 2016.
RCE and Response to Final Office Action for U.S. Appl. No. 14/081,504, dated Dec. 9, 2016.
Response to Non Final Office Action for U.S. Appl. No. 14/152,626, dated Dec. 7, 2016.
Response to Non Final Office Action for U.S. Appl. No. 14/207,344, dated Dec. 9, 2016.
Applicant-Initiated Interview Summary dated Sep. 19, 2016. In U.S. Appl. No. 14/044,050.
Applicant-Initiated Interview Summary dated Sep. 19, 2016, in U.S. Appl. No. 14/152,626.
Non-Final Office Action dated Sep. 9, 2016, in U.S. Appl. No. 14/207,344.
Certification and Request for Consideration Under the After Final Consideration Pilot Program and Amendment C and Response to Final Office Action, filed Oct. 31, 2016 for U.S. Appl. No. 14/331,400.
Response to Non-Final Office Action, filed Oct. 31, 2016, for U.S. Appl. No. 14/081,715.
Arguments in Support of Pre-Appeal Brief Request for Review, filed Nov. 8, 2016 for U.S. Appl. No. 14/044,050.
Non-Final Office Action dated Oct. 26, 2016 for U.S. Appl. No. 13/742,077.
Japanese Office Action dated Sep. 16, 2016 (with translation). issued in Japanese patent application No. 2015252820.
Non-Final Office Action dated Oct. 6, 2016, issued in U.S. Appl. No. 13/742,025.
Non-Final Office Action dated Oct. 7, 2016. issued in U.S. Appl. No. 14/852,656.
Non-Final Office Action dated Oct. 6, 2016, issued in U.S. Appl. No. 13/360,444.
Final Office Action dated Sep. 23, 2016, issued in U.S. Appl. No. 14/152,590.
Final Office Action dated Sep. 27, 2016, issued in U.S. Appl. No. 13/827,790.
Non-Final Office Action dated Aug. 26, 2016. In U.S. Appl. No. 14/858,619.
Amendment & Response to Office Action filed Aug. 29, 2016, in U.S. Appl. No. 13/446,300.
Preliminary Amendment filed Jul. 28, 2016, in U.S. Appl. No. 15/069,989.
Response to Restriction Office Action filed Jul. 28, 2016, in U.S. Appl. No. 14/852,656.
European Office Action dated Jul. 22, 2016. In European patent application No. 10807287.7.
European Office Action dated Jul. 22, 2016. In European patent application No. 10807285.1.
Final Office Action dated Jul. 29, 2016. In U.S. Appl. No. 14/331,400.
Notice of Allowance dated Jul. 11, 2016, in U.S. Appl. No. 13/826,618.
Final Office Action dated Feb. 26, 2015, from U.S. Appl. No. 14/152,590.
Notice of Allowance dated Sep. 3, 2015, from U.S. Appl. No. 13/787,327.
Notice of Allowability dated Sep. 24, 2015, from U.S. Appl. No. 13/787,327.
Notification Concerning Transmittal of International Preliminary Report on Patentability (Chapter 1 of the PCT) dated Sep. 24, 2015, from International Application No. PCT/US2014/024868.
International Preliminary Report on Patentability (Chapter I of the PCT) dated Sep. 15, 2015, from International Application No. PCT/US2014/023416.

(56) References Cited

OTHER PUBLICATIONS

International Preliminary Report on Patentability (Chapter I of the PCT) dated Jul. 30, 2013, from International Application No. PCT/US2012/023006.
Notification of Transmittal of the International Search Report & The Written Opinion of the Internaional Searching Authority, or the Declaration dated Dec. 3, 2013, from International Application No. PCT/US2013/060172.
Supplementary European Search Report & Opinion dated Jun. 25, 2015, from European patent application No. 12739348.6.
Amendment and Response to Office Action filed May 18, 2016 in U.S. Appl. No. 14/081,504.
RCE and Amendment and Response to Final Office Action filed May 23, 2016 in U.S. Appl. No. 13/742,077.
RCE and Amendment and Response to Final Office Action filed May 23, 2016 in U.S. Appl. No. 14/152,626.
Response to Office Action filed May 4, 2016, in U.S. Appl. No. 13/749,823.
Response to Office Action filed Apr. 11, 2016, in U.S. Appl. No. 14/152,590.
Chinese Office Action dated Apr. 25, 2016, in Chinese patent application No. 201380017906.8 (including translation).
Chinese Office Action dated Feb. 24, 2016, in Chinese patent application No. 201410312160X (including translation).
Response to Office Action filed Mar. 21, 2016. in U.S. Appl. No. 13/826,618.
Non-Final Office Action dated Mar. 28, 2016. in U.S. Appl. No. 13/446,300.
Non-Final Office Action dated Mar. 28, 2016. in U.S. Appl. No. 13/827,790.
Non-Final Office Action dated Aug. 10, 2015, from U.S. Appl. No. 14/044,050.
Non-Final Office Action dated Jul. 29, 2015, from U.S. Appl. No. 14/152,626.
RCE & Response to Office Action filed on Aug. 4, 2015, from U.S. Appl. No. 13/360,444.
Chinese Office Action dated Jul. 21, 2015, from Chinese patent application No. 201380006868.6.
Statement of Substance of Telephone Interview dated Mar. 12, 2012 in U.S. Appl. No. 12/689,334.
Applicant-Initiated Interview Summary dated Mar. 6, 2012 in U.S. Appl. No. 12/689,334.
Non-Final Office Action dated Feb. 16, 2012 in U.S. Appl. No. 12/689,334.
Non-Final Office Action dated Mar. 23, 2011 in U.S. Appl. No. 12/689,334.
Response dated Feb. 28, 2012 to Non-Final Office Action in U.S. Appl. No. 12/689,334.
Response dated May 9, 2011 to Non-Final Office Action in U.S. Appl. No. 12/689,334.
Amendment under 37 C.F.R. 1.312 dated Jul. 23, 2012 in U.S. Appl. No. 12/852,989.
Non-Final Office Action dated Feb. 13, 2012 in U.S. Appl. No. 12/852,989.
Response dated Apr. 26, 2012 to Non-Final Office Action in U.S. Appl. No. 12/852,989.
Amendment under 37 C.F.R. 1.312 dated Jul. 23, 2012 in U.S. Appl. No. 12/825,993.
Non-Final Office Action dated Feb. 9, 2012 in U.S. Appl. No. 12/852,993.
Response dated May 3, 2012 to Non-Final Office Action in U.S. Appl. No. 12/852,993.
Non-Final Office Action dated Nov. 2, 2012 in U.S. Appl. No. 13/272,412.
Response dated Aug. 5, 2013 to Non-Final Office Action in U.S. Appl. No. 13/272,412.
Response dated Feb. 1, 2013 to Non-Final Office Action in U.S. Appl. No. 13/272,412.
Non-Final Office Action dated May 3, 2013 in U.S. Appl. No. 13/272,412.
Non-Final Office Action dated Mar. 18, 2015 in U.S. Appl. No. 13/564,925.
Advisory Action dated Nov. 18, 2014 in U.S. Appl. No. 13/564,927.
Final Rejection dated Sep. 3, 2014 in U.S. Appl. No. 13/564,927.
Applicant-Initiated Interview Summary dated Nov. 13, 2014 in U.S. Appl. No. 13/564,927.
Non-Final Office Action dated Mar. 21, 2014 in U.S. Appl. No. 13/564,927.
Response dated Jun. 19, 2014 to Non-Final Office Action in U.S. Appl. No. 13/564,927.
Response dated Nov. 4, 2014 to Final Rejection in U.S. Appl. No. 13/564,927.
Response dated Nov. 25, 2014 to Final Rejection and Advisory Action and Pilot Program Request in U.S. Appl. No. 13/564,927.
Response dated Dec. 17, 2014 to Final Rejection and Second Advisory Actior in U.S. Appl. No. 13/564,927.
Response resubmission dated Nov. 4, 2014 with Pilot Program Request in U.S. Appl. No. 13/564,927.
Second Advisory Action dated Dec. 12, 2014 with Interview Summary in U.S. Appl. No. 13/564,927.
Final Rejection dated Dec. 29, 2014 in U.S. Appl. No. 13/625,548.
Non-Final Office Action dated Jun. 13, 2014 in U.S. Appl. No. 13/625,548.
Response dated Sep. 15, 2014 to Non-Final Office Action in U.S. Appl. No. 13/625,548.
Non-Final Office Action dated Jul. 8, 2015 in U.S. Appl. No. 13/743,668.
Non-Final Office Action dated Jul. 2, 2014 in U.S. Appl. No. 13/803,892.
Non-Final Office Action dated Aug. 5, 2014 in U.S. Appl. No. 13/827,886.
Response dated Dec. 2, 2014 to Non-Final Office Action in U.S. Appl. No. 13/827,886.
Non-Final Office Action dated May 7, 2015 in U.S. Appl. No. 13/827,886.
Final Rejection dated May 21, 2014 in U.S. Appl. No. 13/957,884.
Applicant-Initiated Interview Summary dated Feb. 12, 2014 in U.S. Appl. No. 13/957,884.
Non-Final Office Action dated Nov. 8, 2013 in U.S. Appl. No. 13/957,884.
Response dated Feb. 4, 2014 to Non-Final Office Action in U.S. Appl. No. 13/957,884.
Response dated Mar. 3, 2014 to Applicant-Initiated Interview Summary in U.S. Appl. No. 13/957,884.
Applicant-Initiated Interview Summary dated Jan. 24, 2014 in U.S. Appl. No. 13/957,884.
Final Rejection dated Sep. 12, 2014 in U.S. Appl. No. 13/957,931.
Non-Final Office Action dated Mar. 21, 2014 in U.S. Appl. No. 13/957,931.
Response dated Jun. 19, 2014 to Non-Final Office Action in U.S. Appl. No. 13/957,931.
Response dated Nov. 12, 2014 to Final Rejection in U.S. Appl. No. 13/957,931 Along with Request for Consideration Under the After Final Pilot Program.
Advisory Action dated Dec. 3, 2014 in U.S. Appl. No. 13/957,931.
Non-Final Office Action dated Mar. 13, 2015 in U.S. Appl. No. 14/331,375.
Non-Final Office Action dated Apr. 21, 2015 in U.S. Appl. No. 14/331,422.
Response dated Jul. 20, 2015 to Non-Final Office Action in U.S. Appl. No. 14/331,422.
Non-Final Office Action dated Nov. 12, 2014 in U.S. Appl. No. 13/446,300.
Response dated Feb. 17, 2015 to Non-Final Office Action in U.S. Appl. No. 13/446,300.
Final Rejection dated May 21, 2015 in U.S. Appl. No. 13/446,300.
Response dated Jul. 21, 2015 to Final Rejection in U.S. Appl. No. 13/446,300.
Non-Final Office Action dated May 11, 2015 in U.S. Appl. No. 14/331,400.
Office Action dated Jul. 20, 2015 in Chinese Patent Application No. 201380017906.8.

(56) References Cited

OTHER PUBLICATIONS

Non-Final Office Action dated Aug. 10, 2015 in U.S. Appl. No. 14/044,050.
RCE and Response to Office Action filed Aug. 4, 2015 in U.S. Appl. No. 13/360,444.
Non-Final Office Action dated May 11, 2015, from corresponding U.S. Appl. No. 14/331,400.
DuPont Tm Teflon PTFE 601A, Product Information. Copyright 2005.
S.V. Gandal and Brothers, Encyclopedia of Polymer Science and Technology, 2010, section Perfluorinated Polymers, Polytetrafluoroethylene.
Final Office Action dated May 22, 2015, from U.S. Appl. No. 13/787,327.
Non-Final Office Action dated Jan. 13, 2015, from U.S. Appl. No. 13/827,790.
Final Office Action dated Feb. 20, 2015, from U.S. Appl. No. 14/044,050.
Final Office Action dated Feb. 4, 2015, from U.S. Appl. No. 13/360,444.
Response to Non-Final Office Action filed Jul. 27, 2015, from U.S. Appl. No. 14/152,590.
Response to Non-Final Office Action filed Jul. 13, 2015, from U.S. Appl. No. 13/827,790.
Response to Non-Final Office Action filed Apr. 10, 2015, from U.S. Appl. No. 13/742,025.
Response to Non-Final Office Action filed Jul. 20, 2015, from U.S. Appl. No. 14/044,050.
Response to Non-Final Office Action filed Nov. 3, 2014, from U.S. Appl. No. 14/044,050.
Applicant-Initiated Interview Summary dated May 8, 2015, from U.S. Appl. No. 13/742,025.
Applicant-Initiated Interview Summary dated May 27, 2015, from U.S. Appl. No. 14/044,050.
Office Action dated Mar. 18, 2015, from corresponding U.S. Appl. No. 13/564,925.
Office Action dated Mar. 13, 2015, from corresponding U.S. Appl. No. 14/331,375.
U.S. Office Action dated Feb. 4, 2015, for U.S. Appl. No. 13/360,444, filed Jan. 27, 2012.
International Preliminary Report on Patentability for PCT Application No. PCT/US2012/023006, filed Jan. 27, 2012.
International Search Report for PCT Application No. PCT/US2012/023006, filed Jan. 27, 2012.
European Search Report dated Aug. 19, 2014 for EP12755426.9.
Final Office Action dated Feb. 22, 2016. in U.S. Appl. No. 13/742,077.
Non-Final Office Action dated Feb. 16, 2016. in U.S. Appl. No. 14/918,877.
Non-Final Office Action dated Feb. 5, 2016. in U.S. Appl. No. 13/749,823.
Amendment & Response to Office Action filed with the USPTO on Feb. 2, 2016, in U.S. Appl. No. 13/742,077.
Amendment & Response to Office Action filed with the USPTO on Feb. 9, 2016. in U.S. Appl. No. 14/044,050.
Non-Final Office Action dated Jan. 12, 2016. in U.S. Appl. No. 14/152,590.
Non-Final Office Action dated Jan. 14, 2016. in U.S. Appl. No. 14/331,400.
Final Office Action dated Jan. 22, 2016, in U.S. Appl. No. 14/152,626.
Non-Final Office Action dated Dec. 18, 2015, in U.S. Appl. No. 14/081,504.
Non-Final Office Action dated Nov. 20, 2015, in U.S. Appl. No. 13/826,618.
Amendment and Response to Office Action filed Nov. 30, 2015 in U.S. Appl. No. 14/152,626.
Non-Final Office Action dated Nov. 30, 2015 in U.S. Appl. No. 14/175,016.
RCE and Amendment B and Response to Final Office Action filed Nov. 20, 2015 in U.S. Appl. No. 13/446,300.
Final Office Action dated Oct. 15, 2015, from U.S. Appl. No. 13/827,790.
Final Office Action dated Oct. 21, 2015, from U.S. Appl. No. 14/331,422.
Supplementary European Search Report dated Oct. 20, 2015, from EP Patent Application No. 13772707.9.
Supplementary European Search Report dated Oct. 22, 2015, from EP Patent Application No. 13741191.4.
Office Action dated Sep. 24, 2015, from EP Patent Application No. 10732230.7.
Non-Final Office Action dated Nov. 2, 2015. from U.S. Appl. No. 13/742,077.
Response to Aug. 29, 2014 Non-Final Office Action, filed with USPTO on Nov. 25, 2014, from U.S. Appl. No. 14/152,590, filed Jan. 10, 2014.
Supplemental Amendment filed Jun. 20, 2016, for U.S. Appl. No. 13/826,618.
Non-Final Office Action dated Jun. 20, 2016 for U.S. Appl. No. 14/348,309.
Non-Final Office Action dated Jun. 9, 2016 for U.S. Appl. No. 14/152,626.
Final Office Action dated Jun. 8, 2016 for U.S. Appl. No. 14/044,050.
Amendment B and Response to Office Action filed Jun. 13, 2016 for U.S. Appl. No. 14/331,400.
Non-Final Office Action dated Jun. 10, 2016 for U.S. Appl. No. 13/749,823.
Final Office Action dated Jun. 16, 2016 for U.S. Appl. No. 14/175,016.
Non-Final Office Action dated Jun. 30, 2016 for U.S. Appl. No. 14/081,715.
Response to Non-Final Office Action filed Jun. 28, 2016 for U.S. Appl. No. 13/827,790.
Supplemental Amendment filed Jun. 28, 2016 for U.S. Appl. No. 13/742,077.
Non-Final Office Action dated Jun. 19, 2017, from U.S. Appl. No. 14/081,504.
Response to Office Action filed Jun. 15, 2017, in U.S. Appl. No. 14/207,344.
Non-Final Office Action dated Jun. 29, 2017, from U.S. Appl. No. 14/081,715.
Final Office Action dated Jun. 27, 2017, from U.S. Appl. No. 13/360,444.
Non-Final Office Action dated Jun. 23, 2017, from U.S. Appl. No. 13/749,823.
Non-Final Office Action dated Jul. 12, 2017, from U.S. Appl. No. 14/331,400.
Xiong, Joe, Fabrication of Ultrafine Fibrous Polytetrafluoroethylene Porous Membranes by Electrospinning. Journal of Materials Research, 24(9), 2755-2761.
Menini, Richard and Masoud Farzaneh, Production of Superhydrophobic Polymer Fibers With Embedded Particles Using the Electrospinning Technique, Polymer International 57:77-84, 2008.
Lee, K.H. et al. The Change of Bead Morphology Formed on Electrospun Polystyrene Fibers, Polymer 44 (2003), p. 4029-4034.
Response to Office Action filed Jul. 7, 2017, in U.S. Appl. No. 13/826,618.
Final Office Action dated Jul. 26, 2017, from U.S. Appl. No. 13/827,790.
Reply Brief filed Aug. 7, 2017, in U.S. Appl. No. 14/044,050.
RCE and Response to Office Action filed Aug. 14, 2017, in U.S. Appl. No. 13/742,025.
Japanese Office Action dated Sep. 1, 2017, issued in corresponding Japanese patent application No. 2015504605.
Final Office Action dated Jun. 1, 2017, from U.S. Appl. No. 14/852,656.
Examiner's Answer dated Jun. 5, 2017, from U.S. Appl. No. 14/044,050.
Response to Office Action filed Jun. 7, 2017. from U.S. Appl. No. 13/827,790.

(56) References Cited

OTHER PUBLICATIONS

Non-Final Office Action dated Mar. 2, 2017. from U.S. Appl. No. 14/636,274.
Non-Final Office Action dated Mar. 9, 2017, from U.S. Appl. No. 15/069,988.
Final Office Action dated Jan. 23, 2017. issued in U.S. Appl. No. 14/081,715.
Notice of Allowance dated Jan. 25, 2017. issued in U.S. Appl. No. 14/152,626.
Non-Final Office Action dated Feb. 7, 2017, issued in U.S. Appl. No. 13/827,790.
Response to Office Action filed Feb. 6, 2017. in U.S. Appl. No. 13/360,444.
Response to Office Action filed Feb. 6, 2017. in U.S. Appl. No. 13/742,025.
Japanese Office Action dated Jan. 17, 2017. in Japanese patent application No. 2015-504605.
Response to Office Action filed Feb. 7, 2017. in U.S. Appl. No. 14/852,656.
Chinese Office Action dated Jan. 22, 2017. in Chinese patent application No. 201380006868.6.
Chinese Office Action dated Jan. 11, 2017, in Chinese patent application No. 201380017906.8.
Applicant Initiated Interview Summary for U.S. Appl. No. 13/826,618 dated Mar. 20, 2017.
Non Final Office Action in U.S. Appl. No. 13/826,618 dated Apr. 7, 2017.
Non Final Office Action in U.S. Appl. No. 14/207,344 dated Mar. 15, 2017.
Non Final Office Action in U.S. Appl. No. 14/631,909 dated Apr. 7, 2017.
Non Final Office Action in U.S. Appl. No. 15/069,989 dated Mar. 23, 2017.
Non Final Office Action in U.S. Appl. No. 14/204,466 dated Mar. 31, 2017.
Response to Non Final Office Action in U.S. Appl. No. 13/742,077 dated Mar. 27, 2017.
Response to Office Action filed Sep. 19, 2017, in U.S. Appl. No. 14/081,504.
Amendment A amd Response to Office Action filed Sep. 19, 2017, in U.S. Appl. No. 15/069,989.
Final Office Action dated Sep. 28, 2017, from U.S. Appl. No. 14/207,344.
Response to Office Action filed Sep. 29, 2017, in U.S. Appl. No. 14/081,715.
Notice of Allowance dated Oct. 4, 2017, in U.S. Appl. No. 14/204,466.
Response to Office Action filed Oct. 4, 2017, in U.S. Appl. No. 13/749,823.
Chinese Office Action dated Sep. 22, 2017, in Chinese Patent Application No. 201380006868.6.
Chinese Response to Office Action filed Oct. 10, 2017, in Chinese Patent Application No. 201410312160X.
Indian Response to Office Action filed Oct. 17, 2017, in Indian Patent Application No. 6058/DELNP/2011.
Final Office Action dated Oct. 16, 2017, from U.S. Appl. No. 13/749,823.
Indian Response to Office Action filed Oct. 20, 2017, in Indian Patent Application No. 1839/KOLNP/2012.
Final Office Action dated Oct. 20, 2017, from U.S. Appl. No. 13/826,618.
RCE and Response to Office Action filed Oct. 25, 2017, in U.S. Appl. No. 13/742,077.
Japanese Office Action dated Oct. 26, 2017, in Japanese Patent Application No. 2014-554841.
Non-Final Office Action dated Nov. 1, 2017, from U.S. Appl. No. 13/446,300.
Rce and Response to Office Action filed Oct. 26, 2017, in U.S. Appl. No. 13/360,444.
Non-Final Office Action dated Nov. 3, 2017, from U.S. Appl. No. 14/967,597.
Non-Final Office Action dated Nov. 17, 2017, from U.S. Appl. No. 13/360,444.
Non-Final Office Action dated Nov. 21, 2017, from U.S. Appl. No. 14/152,590.
Response to Final Office Action filed Nov. 27, 2017, in U.S. Appl. No. 13/827,790.
Non-Final Office Action dated Dec. 28, 2017, from U.S. Appl. No. 13/827,790.
Final Office Action dated Dec. 29, 2017, from U.S. Appl. No. 14/081,504.
Non-Final Office Action dated Dec. 28, 2017, from U.S. Appl. No. 14/858,556.
Final Office Action dated Dec. 28, 2017, from U.S. Appl. No. 15/069,989.
Final Office Action dated Jan. 16, 2018, from U.S. Appl. No. 14/081,715.
Response to Restriction Office Action filed Jan. 23, 2018, from U.S. Appl. No. 15/209,808.
Response to Official Communication filed Jan. 15, 2018 in corresponding Indian patent application No. 1839/KOLNP/2012.
Response to Official Communication filed Nov. 16, 2017 in corresponding Indian patent application No. 526/DELNP/2012.
Response to Official Communication filed Dec. 4, 2017 in corresponding Japanese patent application No. 2015252820.
RCE and Response to Final Office Action filed Jan. 29, 2018, from U.S. Appl. No. 14/207,344.
Response Filed Feb. 7, 2018, in Chinese Patent Application No. 201380006868.6.
Response to Non-Final Office Action filed Feb. 20, 2018, from U.S. Appl. No. 13/360,444.
Non-Final Office Action dated Feb. 16, 2018, from U.S. Appl. No. 13/742,077.
Notice of Allowance dated Mar. 7, 2018, from U.S. Appl. No. 13/742,025.
Response Filed Mar. 7, 2018, in Japanese Patent Application No. 2015-504605.
Response Filed Feb. 28, 2018, in Japanese Patent Application No. 2014-554841.
Response to Communication to Rule 70(2) and 70a(2) of Nov. 6, 2015 in co-pending EP application No. 13772707.9.

\* cited by examiner

COMPOSITE PROSTHETIC DEVICES

CROSS-REFERENCE TO RELATED APPLICATIONS

The present application is a continuation of U.S. patent application Ser. No. 13/803,892, filed Mar. 14, 2013; which application claims priority to U.S. provisional patent application No. 61/620,633, filed Apr. 5, 2012 and U.S. provisional patent application No. 61/724,731, filed Nov. 9, 2012, all of which are incorporated herein by reference in their entireties.

FIELD OF THE INVENTION

The invention is generally related to prosthetic devices and to methods of making and using such prosthetic devices.

BACKGROUND

The successful use of extruded tubes of expanded polytetrafluoroethylene (ePTFE) as synthetic implantable vascular prostheses or tubular grafts is well known and documented. ePTFE, which has been validated through numerous clinical studies, is particularly suited for this purpose as it exhibits superior bio-compatibility and can be mechanically manipulated to form a well-defined porous microstructure known to promote endothelialization. Further, ePTFE has been proven to exhibit a low thrombogenic response in vascular applications. When seeded or infused with an active agent, the microporous structure of ePTFE, comprising nodes and fibrils, controls natural tissue ingrowth and cell endothelialization when implanted in the vascular system. This ability contributes to patency of the tubular graft and long term healing.

In U.S. Pat. No. 6,436,135 to Goldfarb, the microstructure of a synthetic vascular prostheses formed of ePTFE is defined by irregularly spaced nodes interconnected by elongated fibrils. The methods by which these types of structures are produced have been known for more than three decades. In such a structure, the distance between the node surfaces spanned by the fibrils is defined as the inter-nodal distance (IND).

An ePTFE-based vascular prosthesis having a specific IND range can be developed with a given porosity and/or pore size range to enhance tissue ingrowth and cell endothelialization along the inner and outer surface of the prosthesis. The IND range is generally small enough to prevent transmural blood flow and thrombosis but is generally not less than the maximum dimension of the average red blood cell (e.g., between about 6 and 8 µm). Vascular prostheses based on ePTFE are thus inherently porous. The porosity of an ePTFE vascular prosthesis is controlled by the mechanical formation of the IND and/or the microporous structure of the tube.

One exemplary vascular prosthesis is a stent, which is a medical device commonly used to restore and maintain body passages, such as blood vessels. Often, biocompatible materials can be provided on the inner and/or outer surfaces of the stent to reduce reactions associated with contact between the stent and the body. However, it is difficult with conventional devices to manipulate certain properties such as mechanical properties, cellular proliferation, cellular permeability, fluid permeability, adhesion to a structural frame, and/or incorporation of one or more active therapeutic components. Although coverings can sometimes be used to alter the properties of devices, stents generally have complex geometries that cannot be readily covered with covering materials such as ePTFE. Thus, a need exists for materials and processes that address these concerns. Specifically, it would be beneficial to provide methods of providing implantable prosthetic devices, including stents, with properties that can be tailored for various purposes.

SUMMARY OF THE INVENTION

In accordance with certain embodiments of the present disclosure, composite prosthetic devices comprising one or more porous layers of electrospun polymeric materials are provided. Such porous layers can be, for example, on the inner diameter surface of a tubular prosthetic device, on the outer diameter surface of a tubular prosthetic device, or on both the inner diameter surface and outer diameter surfaces of a tubular prosthetic device. Composite devices can be provided having 2 layers, 3 layers, 4 layers, 5 layers, or more. In certain embodiments, a structural frame (e.g., a stent or other device) can be incorporated within the structure. At least one layer within the composite prosthetic device can, in some embodiments, comprise electrospun poly(tetrafluoroethylene) (PTFE). Advantageously, in certain embodiments, the composite prosthetic device exhibits some degree of porosity.

In one aspect of the disclosure is provided a multi-layered tubular composite prosthetic device comprising at least one porous layer comprising electrospun poly(tetrafluoroethylene) and at least one porous layer comprising a second electrospun polymer. The makeup of the second electrospun polymer can be, for example, a solution-electrospun polymer (e.g., a thermoplastic polymer or a thermoset polymer, such as polyurethane, a silicone (e.g., PDMS), polyether block amide (PEBA), a polyamide, ultra-high molecular weight polyethylene (UHMWPE), a polyester, fluorinated ethylene propylene (FEP), polyvinylidene fluoride (PVDF), perfluoroalkoxy (PFA), a tetrafluoroethylene/hexafluoropropylene/vinylidene fluoride copolymer (THV), poly(ethylene-co-tetrafluoroethylene) (ETFE), ethylene chlorotrifluoroethylene (ECTFE), PCTFE (polychlorotrifluoroethylene), or a copolymer, blend, or derivatives thereof). In other embodiments, the second electrospun polymer can be a dispersion-electrospun polymer, e.g., poly(tetrafluoroethylene). Advantageously, in some embodiments, the porous layer comprising a second electrospun polymer penetrates the pores of the porous layer comprising electrospun poly(tetrafluoroethylene).

Although the second electrospun polymer as described herein typically exhibits some degree of porosity, for certain applications, it may be desirable to provide one or more non-porous layers. Such non-porous layers may in some embodiments, be prepared by electrospinning or by other methods as described herein. Accordingly, in certain embodiments of the application are provided a multi-layered tubular composite prosthetic device comprising at least one porous layer comprising electrospun poly(tetrafluoroethylene) and at least one non-porous layer comprising a second electrospun polymer. The preparation and use of non-porous as well as porous electrospun polymers will be described more thoroughly herein.

In certain embodiments, the composite prosthetic devices described herein can further comprise a structural frame (e.g., a stent). Preferably, such structural frames can comprise open spaces and, in some embodiments, the second electrospun polymer can penetrate through the open spaces of the structural frame.

The number of layers of the devices described herein can vary. In some embodiments, a device is provided which comprises at least two porous layers comprising electrospun poly(tetrafluoroethylene). In some embodiments, a device is provided which comprises at least two porous layers comprising the second electrospun polymer. In certain embodiments, at least one of the inner diameter and the outer diameter of the tubular device comprises a porous layer comprising electrospun poly(tetrafluoroethylene). In certain embodiments, the device can further comprise a non-porous polymeric layer.

Certain specific embodiments are described as follows. In one embodiment is provided a tubular composite prosthetic device, wherein the cross-section of the device comprises: a lumen surrounded by a first porous layer comprising electrospun poly(tetrafluoroethylene) on the device inner diameter surface; a structural frame embedded in the porous layer comprising electrospun poly(tetrafluoroethylene); a second porous layer comprising electrospun poly(tetrafluoroethylene) on the device outer diameter surface; and a third layer between said first and second layers, comprising a different electrospun polymer.

In one embodiment is provided a tubular composite prosthetic device, wherein the cross-section of the device comprises: a lumen surrounded by a first porous layer comprising electrospun poly(tetrafluoroethylene) on the inner diameter surface; a structural frame embedded in the porous layer comprising electrospun poly(tetrafluoroethylene); a second porous layer comprising electrospun poly(tetrafluoroethylene) on the device outer diameter surface; and at least two alternating layers of electrospun poly(tetrafluoroethylene) and a different electrospun polymer, between said first and second layers.

In another embodiment is provided a tubular composite prosthetic device, wherein the cross-section of the device comprises: a lumen surrounded by a first porous layer comprising electrospun poly(tetrafluoroethylene) on the device inner diameter surface; a structural frame embedded in the porous layer comprising electrospun poly(tetrafluoroethylene); and a second porous layer comprising a second electrospun polymer on the device outer diameter surface.

In a further embodiment is provided a tubular composite prosthetic device, wherein the cross-section of the device comprises: a lumen surrounded by a first porous layer comprising electrospun poly(tetrafluoroethylene) on the device inner diameter surface; a structural frame situated around and adjacent to said first porous layer; a second porous layer comprising electrospun poly(ethylene terephthalate) on the device outer diameter surface; and a third layer between said structural frame and said second layer comprising a different electrospun polymer, wherein the structural frame comprises open spaces through which the different electrospun polymer penetrates.

In a still further embodiment is provided a tubular composite prosthetic device, wherein the cross-section of the device comprises: a lumen surrounded by a first porous layer comprising electrospun poly(tetrafluoroethylene) on the device inner diameter surface; a structural frame situated around and adjacent to said first porous layer; a second porous layer comprising electrospun poly(tetrafluoroethylene) on the device outer diameter surface; and at least two alternating layers of electrospun poly(tetrafluoroethylene) and a different electrospun polymer between said first and second layers, wherein a layer comprising the different electrospun polymer is adjacent to the structural frame and the structural frame comprises open spaces through which the different electrospun polymer penetrates.

In one additional embodiment is provided a tubular composite prosthetic device, wherein the cross-section of the device comprises: a lumen surrounded by a first porous layer comprising electrospun poly(tetrafluoroethylene) on the device inner diameter surface; a second porous layer comprising electrospun poly(tetrafluoroethylene) on the device outer diameter surface; and a third layer between said first and second layers, comprising a different electrospun polymer, wherein a structural frame is embedded in the third layer.

In another aspect of the invention is provided a method for producing a composite prosthetic device comprising: combining at least one porous layer comprising electrospun poly(tetrafluoroethylene) and at least one porous layer comprising a second electrospun polymer to give a composite prosthetic device precursor; and applying pressure, heat, or both pressure and heat to the composite prosthetic device precursor to provide a composite prosthetic device.

The combining step can, in some embodiments, comprise wrapping the porous layer comprising the second electrospun polymer around the porous layer comprising the electrospun poly(tetrafluoroethylene). The combining step can, in some embodiments, comprise electrospinning the porous layer comprising a second electrospun polymer onto the porous layer comprising electrospun poly(tetrafluoroethylene).

The methods described herein can provide composite prosthetic devices with varying compositions and properties. In some embodiments, the second electrospun polymer comprises a solution-electrospun polymer. In some embodiments, the second electrospun polymer comprises unsintered poly(tetrafluoroethylene). Advantageously, where the composite device comprises unsintered poly(tetrafluoroethylene), the method further comprises sintering the composite prosthetic device following the applying step.

The applying step can, in some embodiments, comprise applying heat, pressure, or both heat and pressure for a time sufficient to result in the penetration of the second electrospun polymer into the pores of the at least one porous layer comprising electrospun poly(tetrafluoroethylene). In some embodiments, heat and pressure are applied sequentially or simultaneously. The pressure and/or temperature can vary. In certain embodiments, the pressure is between about 200 and about 2000 PSI (e.g., between about 500 PSI and about 1500 PSI) and the temperature is between about 100° C. and about 400° C. The applying step can be conducted, for example, in a pressure vessel. Further exemplary discussion of materials and methods as disclosed herein is provided in U.S. provisional patent application No. 61/620,633, filed Apr. 5, 2012 and U.S. provisional patent application No. 61/724,731, filed Nov. 9, 2012, which are both incorporated herein by reference in their entireties.

BRIEF DESCRIPTION OF THE DRAWINGS

A full and enabling disclosure, directed to one of ordinary skill in the art, is set forth more particularly in the remainder of the specification, which makes reference to the appended figures in which.

DETAILED DESCRIPTION OF THE INVENTION

Figure 1:
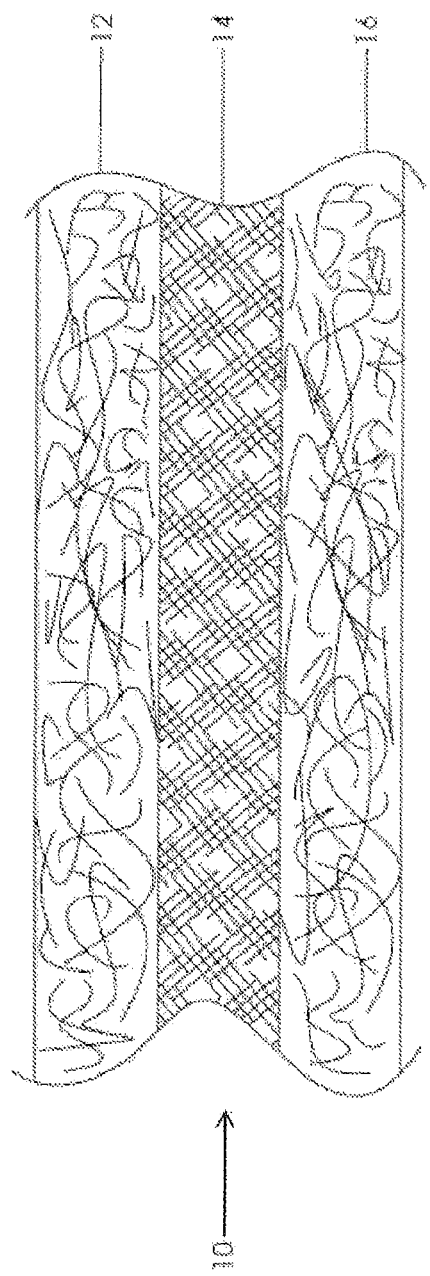
FIG. 1 is a schematic cross-sectional view of a wall of a mono-component composite device in accordance with the present disclosure.

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Each example is provided by way of explanation of the disclosure, and is not intended to be limiting of the disclosure. In fact, it will be apparent to those skilled in the art that various modifications and variations can be made in the present disclosure without departing from the scope or spirit of the invention. For instance, features illustrated or described as part of one embodiment can be used in the context of another embodiment to yield a further embodiment. Thus, it is intended that the present disclosure covers such modifications and variations as come within the scope of the disclosed embodiments and their equivalents.

Overview of Composite Prosthetic Devices According to the Present Disclosure

Generally, the present disclosure provides composite prosthetic devices comprising one or more layers of electrospun (also referred to herein as "espun") fibers around a central lumen and methods of preparation thereof, wherein at least one layer comprises a dispersion-spun polymer. In some embodiments, the one or more layers of espun fibers can comprise the inner diameter surface, the outer diameter surface, or both the inner and outer diameter surfaces of a tubular composite prosthetic device. The focus of the application is on multi-layered structures comprising at least one layer of espun fibers on the inner diameter surface and at least one layer of espun fibers on the outer diameter surface; however, the disclosure is intended to also relate to structures comprising only one of these. For example, a structural frame having a single layer of espun fibers on the inner diameter surface is intended to be encompassed by the present disclosure and a structural frame having a single layer of espun fibers on the outer diameter surface is also intended to be encompassed by the present disclosure.

The composite prosthetic devices described herein can, in certain embodiments, offer a number of advantages over conventional devices. For example, in certain embodiments, the composite prosthetic devices provided herein advantageously exhibit one or more of: 1) the ability to incorporate layers with vastly different pore structures and sizes (allowing for the manipulation of various properties such as mechanical properties, cellular proliferation, cellular permeability, fluid permeability, adhesion to a structural frame, and/or possible incorporation of one or more active therapeutic components within different structural layers); 2) the ability to make a composite construction comprising at least two different components (even vastly different components, thus enabling a broad range of therapeutic uses and structures); 3) improved bonding between various layers, including the one or more espun layers, the optional structural frame, and/or other optional layers of the composite device; 4) the inclusion of a material (e.g., electrospun poly(tetrafluoroethylene) (PTFE)) that closely mimics that of the extracellular matrix, thus affording greater control of cellular response; and 5) the ability to provide a covering (layer) on devices having both simple and complex geometries, which can pose a challenge for covering with conventional materials.

The type of prosthetic device provided according to the present invention can vary and the device can be tailored so as to be used for any given purpose. Generally, prosthetic devices as intended herein are tubular prosthetic devices. By "tubular prosthetic device" is meant that the device has a 3-dimensional shape and this term is intended to cover devices of varying sizes (e.g., length, thickness, and/or diameter), shapes, and compositions. Such tubular prosthetic devices are generally characterized as having a central lumen. A tubular prosthetic device can generally be described as having both an inner diameter ("ID") and an outer diameter ("OD"). "Tubular devices" is intended to be broadly construed to include stents, grafts, and stent grafts having typical cylindrical-shaped structures as well as structures having shapes including, but not limited to, non-linear-shaped, petal-shaped, saddle-shaped, Y-shaped, mushroom-shaped, flared shaped, bell-shaped, single horn-shaped, double horn-shaped, hourglass-shaped, single cup-mouth shaped, twin cup-mouth shaped, cup mouth-ball shaped, and the like. One or both ends of the prosthetic device can be coiled or otherwise shaped to prevent migration of the device within the body.

Generally, prosthetic devices are devices that can be placed into an artery, blood vessel, or other duct to hold the duct open or to redirect blood flow within the duct, or the like. In certain embodiments, the present disclosure is directed to vascular prosthetic devices (also referred to herein as "vascular prostheses"). Such devices can be vascular stents or vascular stent grafts. Representative vascular prostheses include coronary stents, coronary artery by-pass grafts, blood vessel stents, artificial by-pass grafts, by-pass shunts, arteriovenous grafts, homografts, pulmonary allografts, and/or pulmonary shunts. Other tubular prosthetic devices that may be provided according to the invention include, but are not limited to, hemodialysis tubes, ureteral stents, urethral or prostatic stents, prostatic/sphincter stents, esophageal stents, laryngeal stents, tracheal stents, biliary stents, duodenal stents, colonic stents, pancreatic stents, tracheobronchial stents, and gastrointestinal stents.

The composite prosthetic devices of the present disclosure can have varying compositions. Generally, the composite prosthetic devices described herein comprise one or more electrospun layers (including two or more electrospun layers). Electrospun layers are understood to be polymeric layers prepared via an electrospinning process as described herein. Electrospun layers typically comprise a plurality of fibers, which in some embodiments are in random orientation with respect to one another. In certain embodiments, electrospun layers can be described as fibrous and/or porous. The diameter of the fibers within an espun mat according to the present disclosure can vary. In certain embodiments, espun layers can comprise fibers having average diameters of at least about 0.01 µm. For example, the average diameter of fibers in each of the one or more espun layers of the composite devices can, in some embodiments, range from about 10 nm to about 2000 nm in size. In some embodiments, one or more of the espun layers, in final form, have fibers deposited in a density such that there is a range of distances of about 0.1 µm to about 50 µm between points of contact.

Further, the pore size of a given layer and of the composite device as a whole can vary. As used herein in reference to the espun layers, "pore size" is intended to refer to effective pore size (rather than actual pore size) as measured, for example, by air flow and/or water flow (e.g., as defined by ASTM F316 Pore Size Characterization by Bubble Point, which is incorporated herein by this reference). It is noted that, given the nature of the espun fiber mats, it is generally not possible to measure actual pore size of such materials using microscopy methods. The effective pore size of a given espun layer within a composite device as described herein can range from about 0.0 µm (e.g., a non-porous film) to about 50 µm, e.g., from about 0.05 µm to about 20 µm. Advantageously, the effective pore size of each layer is greater than about 0.0 µm as, in certain embodiments, it is desired to provide a composite device exhibiting some degree of porosity. It is noted that, in some embodiments, the effective pore size of a given layer may not be accurately known, such as, for example, where layers are applied and subsequently compressed and/or sintered within the composite device.

In some embodiments, the individual layers comprising a composite prosthetic device as described herein can have varying thicknesses. For example, in some embodiments, each layer can have an average thickness ranging from about 0.0001 inches to about 0.25 inches. In some embodiments, layers with thicknesses at the low end of this range are desirable (e.g., about 0.0001 inches to about 0.0010 inches, such as about 0.0003 inches to about 0.0005 inches) The thickness of a given layer can depend, in part, on the method of preparation of the layer and on the makeup of the layer. For example, in some embodiments, very thin espun layers of PU (e.g., between about 0.0001 inches and about 0.0005 inches) are readily obtained. Very thin espun layers of PTFE (e.g., about 0.0001 inches) are generally achieved only through direct application to a construct (i.e., by spin coating, as described below) although sheets of PTFE for lamination onto constructs as described herein may, for example, be prepared with thicknesses as low as about 0.0005 inches. Sheets or tubes prepared by electrospinning typically cannot exhibit such low thicknesses and generally exhibit thicknesses of about 0.0008 inches or greater. In preferred embodiments, the thickness of a given layer is relatively uniform throughout. The thickness of a given layer can also depend on the method by which the composite device is produced. For example, a polymeric sheet can be wrapped once, twice, three times, four times, five times, or more times around the device (or on the interior of the device) to obtain varying thicknesses of that layer.

Given this range of possible layer thicknesses, the wall thickness of the composite devices disclosed herein can vary accordingly, depending on the number of layers and on the thickness of each layer. For example, based on the layer thicknesses noted above, a 2-layer composite device can have a wall thickness ranging from about 0.0002 inches to about 0.50 inches, such as from about 0.001 inches to about 0.05 inches, including from about 0.003 inches to about 0.02 inches. It is to be understood that layers of varying thicknesses can be combined within the device. In preferred embodiments, the overall wall thickness of the composite device is relatively uniform throughout the length of the device and around the circumference of the device. However, in embodiments comprising a structural frame, the frame typically comprises an open structure formed from wires or struts and having spaces in between, and it is noted that the wire or strut diameter can impact the wall thickness where the wire or strut is present. Thus, for example, in considering the uniformity of a given composite, the layer thickness at one position on a composite must be compared to the layer thickness at a comparable position on that composite (i.e., by comparing a point at which the wire or strut is present with another point at which the wire or strut is present, or by comparing two points at which the wire or strut is not present). Further, it is understood that, in some embodiments, a seam may be present where one or more layers is wrapped around the device, which can be dependent on the processing conditions used to produce the composite device. Accordingly, in some embodiments, there may be one or more indentations (e.g., lines) or raised portions (e.g., lines) on the outer diameter surface of the device, and such embodiments are intended to be encompassed by "substantially uniform" as described herein.

The overall outer diameter of the device can vary. For example, the overall outer diameter can, in certain embodiments, range from about 0.005 inches to about 2 inches, although larger and smaller composites can be prepared without departing from the present disclosure. The final length can vary greatly as the composites can be produced as sheets or tubes at continuous roll lengths.

The composite devices described herein can have varying numbers of polymeric layers (e.g., 2-layered, 3-layered, 4-layered, 5-layered, 6-layered, 7 layered, 8-layered, 9-layered, 10-layered, or having even more layers). In certain embodiments, a layer on the inner diameter surface of a composite device may comprise between about 1 and about 5 wrappings (e.g., about 2 wrappings). In certain embodiments, a layer on the outer diameter surface of a composite device may comprise between about 2 and about 10 wrappings (e.g., about 4-8 wrappings or about 5-7 wrappings). It is noted that, although the components of the composite prosthetic devices described herein are described as comprising "layers," these layers may not always be discrete layers. For example, although layers are advantageously continuous layers, in some embodiments, they may not always be continuous layers. Further, in some embodiments, the composites may exhibit some ingress of one "layer" into another "layer." These scenarios are still intended to be encompassed by the term "layered."

Generally, at least one layer within the composite prosthetic devices described herein functions as a "tie layer." A tie layer is a layer that is incorporated into the composite device in a form such that it serves to adhere and/or bond two or more layers together. To fulfill this requirement, the tie layer component must exhibit some degree of flow, tackiness, and/or moldability at ambient temperature and/or at elevated temperature when it is incorporated within the device. Typically, a composite prosthetic device precursor, comprising all layers to be included in the final device, is prepared and the precursor is treated before use (i.e., by applying heat and/or pressure) such that the tie layer may not maintain these properties in the final composite device provided herein. In some embodiments, the tie layer comprises the same polymer type as the one or more layers adjacent thereto and, in some layers, the tie layer comprises a different polymer type. The tie layer can comprise, for example, any of the polymer types and in certain embodiments, may comprise PTFE, PU, or a silicone (e.g., PDMS). In certain embodiments, the tie layer penetrates the pores of one or both of the layers with which it is in contact and thus can provide a mechanical-type connection between the layers. In certain embodiments, the tie layer advantageously can penetrate at least a portion of the open spaces in a structural frame, where present. Where a frame is present, a tie layer may, in some embodiments, serve to connect and/or bond the material comprising the inner diameter surface of the composite device to the outer diameter surface (e.g., through the structural frame). The incorporation of such a layer will be described in greater detail herein.

As the presently described devices comprise two or more polymeric layers, a wide range of composite devices having varying properties are provided. By incorporating layers with different properties (e.g., composition, thickness, effective pore size, fiber size, etc.), devices with various combinations of properties are afforded. Means for adjusting these and other properties are described further herein. Further, the chemical makeup of the individual layers can provide an additional degree of tailoring. Due to the layered, "sandwich"-type construction of the composite devices of the present disclosure, physical properties such as thickness and pore size can vary from layer to layer within the cross section of the composite device, depending on the construction. An example would be an asymmetrical construction where pores change in size from large to small based on layer evaluations from surface to surface throughout the material.

As noted, the specific compositions of the composite prosthetic devices provided according to the present disclosure can vary, as described in greater detail herein. However, in all composite prosthetic devices disclosed herein, at least one layer of the device generally comprises a fibrous mat prepared via dispersion-based electrospinning (i.e., a "dispersion-spun component"). Exemplary materials and methods involved in dispersion-based electrospinning are described in greater detail below.

In certain embodiments, the fibrous mat prepared via dispersion-based electrospinning (i.e., the dispersion-spun component) is an electrospun fibrous mat comprising a fluorinated polymer (e.g., poly(tetrafluoroethylene) (PTFE)). Although much of the description of electrospinning provided herein focuses specifically on electrospinning PTFE and on electrospun mats comprising PTFE, it is noted that the methods and materials described herein may employ an alternative polymer in place of the PTFE. Exemplary fluorinated polymers that can be incorporated as a dispersion-spun component of the composite prosthetic devices described herein include, but are not limited to, fluorinated ethylene propylene (FEP), polyvinylidene fluoride (PVDF), perfluoroalkoxy (PFA), a copolymer of tetrafluoroethylene, hexafluoropropylene and vinylidene fluoride (THV), poly(ethylene-co-tetrafluoroethylene) (ETFE), ethylene chlorotrifluoroethylene (ECTFE), PCTFE (polychlorotrifluoroethylene), and copolymers, blends, and derivatives thereof. Further, although the application as written is directed to embodiments wherein the dispersion-spun component comprises a fluorinated polymer, it is noted that other polymers that can be spun from a dispersion can alternatively or additionally be employed as a dispersion-spun component.

In some embodiments, a composite prosthetic device is provided wherein the two or more electrospun layers consist of one type of material, i.e., the same type of material (giving a "mono-component composite" prosthetic device), optionally in combination with a structural frame (e.g., a stent). In such embodiments, the composite prosthetic device comprises two or more layers of a dispersion-spun polymeric component. The tie layer of such devices thus consists of the same type of polymeric material as that of the one or more additional layers. For example, in one particular embodiment, an electrospun PTFE-based composite device is provided, wherein each of the two or more polymeric layers of the composite prosthetic device comprises electrospun PTFE. In such embodiments, the properties (e.g., thickness, pore size, fiber diameter, etc.) of each layer can vary such that different PTFE layers of the composite device can exhibit different properties. Although PTFE is exemplified, it is noted that other prosthetic composites consisting of or consisting essentially of one polymeric material other than PTFE may also be provided according to the present disclosure.

Figure 2:
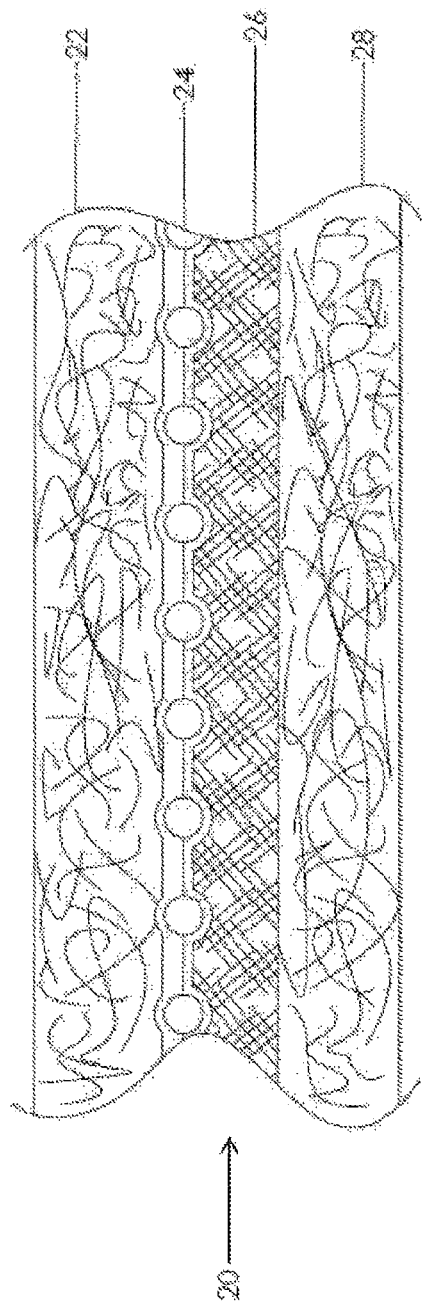
FIG. 2 is a schematic cross-sectional view of a wall of a mono-component composite device comprising a structural frame in accordance with the present disclosure.

Exemplary mono-component composite prosthetic devices are illustrated in FIGS. 1 and 2. FIG. 1 illustrates a cross-sectional view of a wall of a composite prosthetic device 10, wherein the coverings on the inner (12) and outer (16) diameter surfaces of the device comprise the same dispersion-spun polymer (e.g., PTFE). Layer 14 is a tie layer, comprising the same type of polymer (e.g., PTFE), but layer 14 is initially incorporated into the structure in unsintered (tacky and moldable) form. It is noted that device 10 will be subjected to heat and/or pressure prior to use to provide layer 14 in sintered, fibrous form and to promote adhesion between layers (e.g., via penetration of layer 14 into the pores of layer 12 and/or layer 16). FIG. 2 illustrates a cross-sectional view of a wall of a composite prosthetic device 20, which is similar but further incorporates a structural frame 24. Again, layers 22, 26, and 28 comprise the same type of polymer (e.g., PTFE) and the tie layer (26) is initially incorporated in unsintered form. Here, the application of heating and pressure to the device precursor preferably causes the tie layer 26 to penetrate through interstices in structural frame 24, as well as into the pores of layer 22 and/or 28. In some embodiments, the application of heating and pressure can cause tie layer 26 to bond the material comprising the inner diameter surface of the composite device to the material comprising the outer diameter surface of the device. Again, the composite device precursor is preferably heated prior to use to provide layer 26 in sintered form in the final composite device (e.g., where the layer comprises PTFE).

In contrast, multi-component composite devices have at least two types of electrospun polymeric layers and can have any number of different types of polymeric materials therein (e.g., at least 2, at least 3, or at least 4). Each polymer type within the multi-component composite devices as described herein can be represented in one layer or more than one layer. For example, a composite device can have: one layer of a given first electrospun material and one layer of a given second electrospun material; two or more layers of a given first electrospun material and one layer of a given second electrospun material; or two or more layers of a given first electrospun material and two or more layers of a given second electrospun material. The multi-component composite devices provided herein, in addition to comprising one or more dispersion-spun layers, comprise one or more additional layers, which can be prepared via dispersion-based electrospinning, melt-based electrospinning, and/or solution-based electrospinning.

In certain embodiments, the one or more additional electrospun layers of the prosthetic device comprise an electrospun thermoplastic or thermoset polymer. A thermoplastic is understood to be any polymer that becomes moldable above a specific temperature and returns to a solid state upon cooling. A thermoset is understood to be a polymeric material that is initially moldable, but can cured (usually irreversibly) to give a solid (e.g., by the application of heat or radiation). In some embodiments, the thermoplastic or thermoset polymer is an elastomer. An elastomer is a polymer that can be repeatedly stretched and/or deformed without permanently deforming the shape thereof.

Certain exemplary polymers that can be incorporated as electrospun layers in the multi-component prosthetic devices disclosed herein are polyurethanes (PU) and silicones, e.g., polydimethylsiloxane (PDMS). Other polymers useful for this purpose include, but are not limited to, polyether block amide (PEBA, e.g., PEBAX®), polyamides, polyethylene (e.g., ultra-high molecular weight polyethylene, UHMWPE), polyesters, and copolymers, blends, and derivatives thereof. Additionally, certain fluorinated polymers such as fluorinated ethylene propylene (FEP), polyvinylidene fluoride (PVDF), perfluoroalkoxy (PFA), a copolymer of tetrafluoroethylene, hexafluoropropylene and vinylidene fluoride (THV), poly(ethylene-co-tetrafluoroethylene) (ETFE), ethylene chlorotrifluoroethylene (ECTFE), PCTFE (polychlorotrifluoroethylene), and copolymers, blends, and derivatives thereof which can be electrospun can be used. Generally, any thermoplastic or thermoset polymer that forms fibers upon electrospinning can be used in this regard as an additional polymeric component (in addition to the one or more dispersion-spun layers). Preferably, the additional polymeric component is selected such that the electrospun mat produced therefrom retains some degree of porosity when it is combined with the other component(s) of the multi-component composite device and when the resulting device precursor is treated (i.e., when it is exposed to elevated temperature and/or pressure) to provide a final composite device. However, in certain embodiments, it may be desirable to provide a final composite device that is non-porous. In such embodiments, one or more polymeric layers is a non-porous layer (which can be prepared in various ways as described herein, including, but not limited to, by electrospinning and/or by film formation).

Certain multi-component devices described herein exhibit enhanced properties relative to commercially available devices and/or to mono-component devices described herein. Properties that may be enhanced in certain embodiments, include, but are not limited to, robustness, flexibility, strength (e.g., radial strength and burst strength), crush/bend/kink resistance, and compression resistance, for example, as evaluated by testing methods including, but not limited to, air flow testing, torsion testing, tension/compression testing, abrasion resistance testing, burst strength testing, WEP testing, radial force expansion testing, kink resistant testing, 3-point bend testing, flex testing, crush resistance testing, recoil testing, and general physical evaluation.

Figure 3:
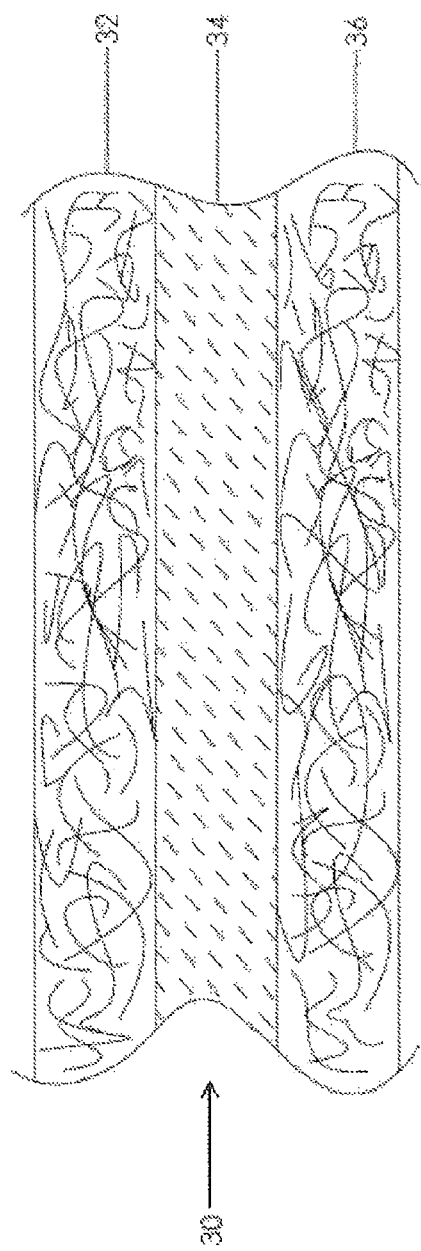
FIG. 3 is a schematic cross-sectional view of a wall of a multi-component composite device in accordance with the present disclosure.
Figure 4:
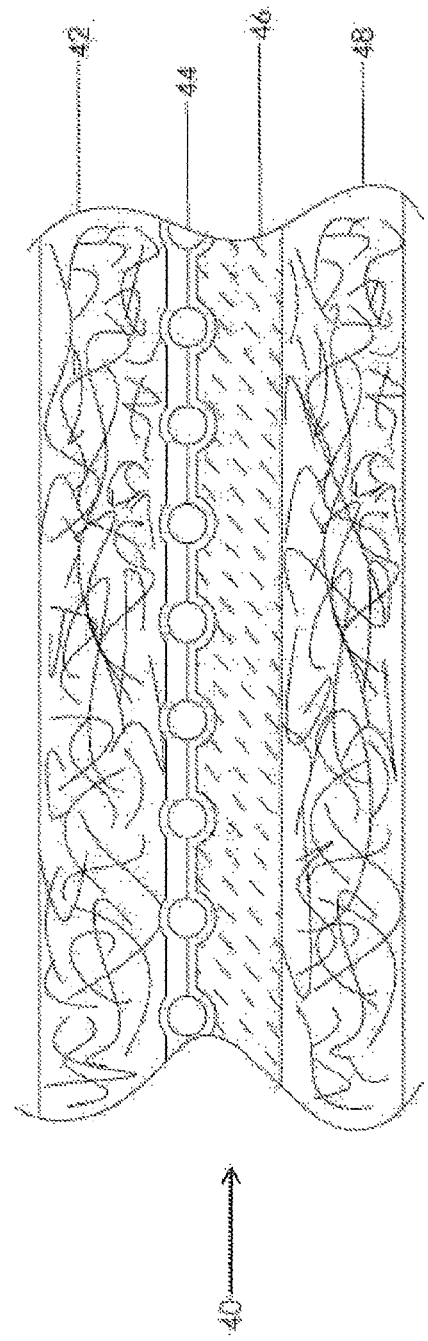
FIG. 4 is a schematic cross-sectional view of a wall of a multi-component composite device comprising a structural frame in accordance with the present disclosure.

Exemplary multi-component composite prosthetic devices are illustrated in FIGS. 3 and 4. FIG. 3 illustrates a cross-sectional view of a wall of a composite prosthetic device 30, wherein the coverings on the inner (32) and outer (36) diameter surfaces of the device comprise the same electrospun polymer (e.g., PTFE). Layer 34 is a tie layer, which comprises a different electrospun polymer than layers 32 and 36 (e.g., PU or PDMS). If layer 34 is a dispersion-spun material, layer 34 is initially incorporated into the structure in unsintered (tacky and moldable) form and must be sintered before the composite device is used. If layer 34 is a solution-spun or melt-spun material, no sintering is required prior to use. However, in all embodiments, the device 30 will be subjected to heat and/or pressure prior to use to promote adhesion between layers (e.g., via penetration of layer 34 into the pores of layer 32 and/or layer 36). FIG. 4 illustrates a cross-sectional view of a wall of a composite prosthetic device 40, which is similar but further incorporates a structural frame 44. Layers 42 and 48 comprise the same electrospun polymer (e.g., PTFE) and the tie layer (46) comprises a different material. Again, if tie layer 46 is a dispersion-spun material, layer 46 is initially incorporated into the structure in unsintered (tacky and moldable) form and must be sintered before the composite device is used. If tie layer 46 is a solution-spun or melt-spun material, no sintering is required prior to use. However, in all embodiments, the device precursor will be subjected to heat and/or pressure prior to use to promote adhesion between layers (e.g., via penetration of layer 46 into the pores of layer 42 and/or layer 48).

Figure 5:
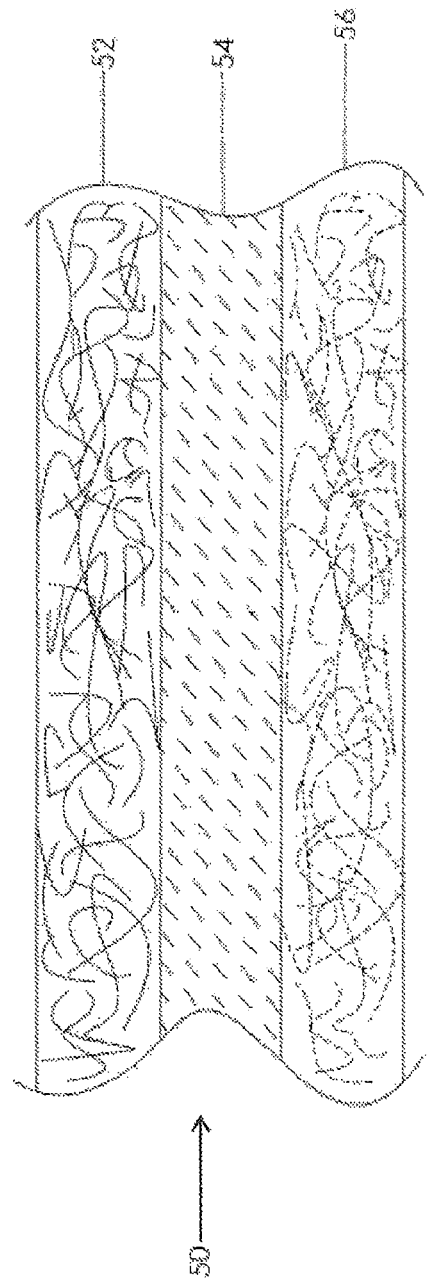
FIG. 5 is a schematic cross-sectional view of a wall of a multi-component composite device in accordance with the present disclosure.
Figure 6:
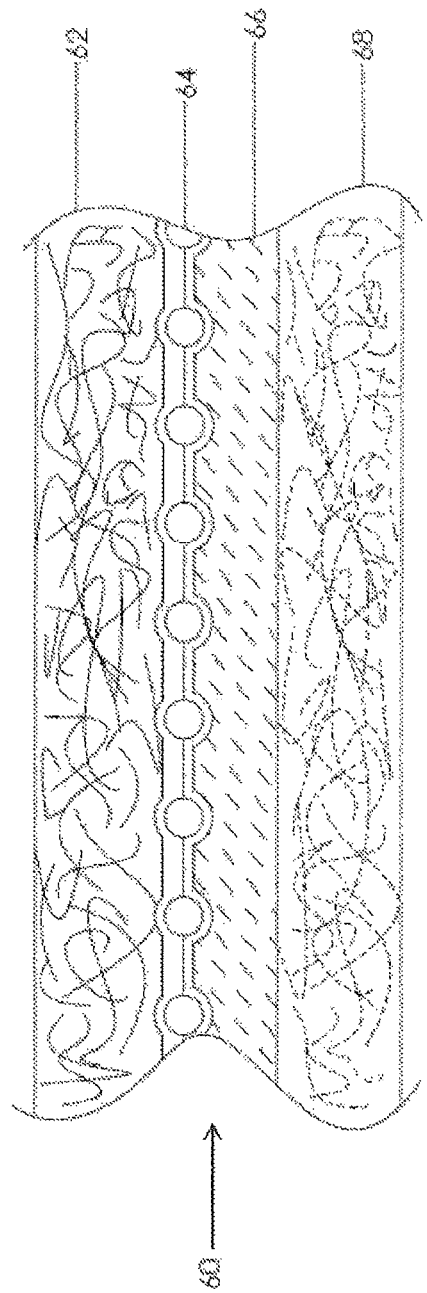
FIG. 6 is a schematic cross-sectional view of a wall of a multi-component composite device comprising a structural frame in accordance with the present disclosure.
Figure 7:
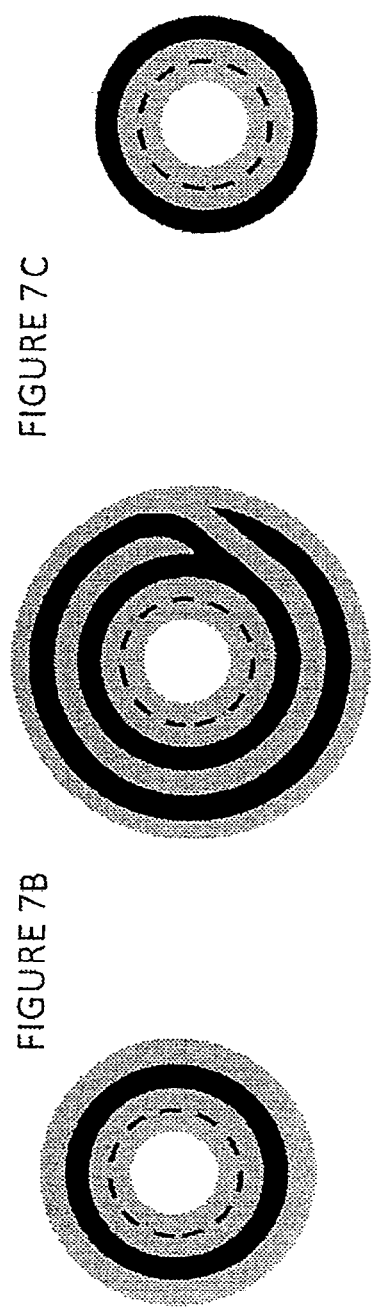
FIGS. 7A-F are schematic cross-sectional views of exemplary multi-component composite devices comprising structural frames in accordance with the present disclosure.

Further exemplary multi-component composite prosthetic devices are illustrated in FIGS. 5 and 6. FIG. 5 illustrates a cross-sectional view of a wall of a composite prosthetic device 50, wherein the coverings on the inner (52) and outer (56) diameter surfaces of the device comprise different polymers. Layer 54 is a tie layer, which may comprise the same polymer as layer 52 or 56 or may comprise a different material. If layer 54 is a dispersion-spun material, layer 54 is initially incorporated into the structure in unsintered (tacky and moldable) form and must be sintered before the composite device is used. If layer 34 is a solution-spun or melt-spun material, no sintering is required prior to use. However, in all embodiments, the device 50 will be subjected to heat and/or pressure prior to use to promote adhesion between layers (e.g., via penetration of layer 54 into the pores of layer 52 and/or layer 56). FIG. 6 illustrates a cross-sectional view of a wall of a composite prosthetic device 60, which is similar but further incorporates a structural frame 64. Layers 62 and 68 comprise different polymers and the tie layer (66) can comprise the same polymer as layer 62 or 68 or may comprise a different material. Again, if tie layer 64 is a dispersion-spun material (e.g., PTFE), layer 64 is initially incorporated into the structure in unsintered (tacky and moldable) form and must be sintered before the composite device is used. If tie layer 64 is a solution-spun or melt-spun material, no sintering is required prior to use. However, in all embodiments, the device precursor will be subjected to heat and/or pressure prior to use to promote adhesion between layers (e.g., via penetration of layer 64 into the pores of layer 62 and/or layer 68).

FIGS. 7A-7F are schematic cross-sections of representative multi-component prosthetic devices according to the present disclosure, having greater than two layers. In each of these embodiments, two polymeric components are present; the grey layers represent the dispersion-spun component (e.g., PTFE) and the black layers represent a different type of polymeric material (e.g., PU or PDMS). The dashed lines represent structural frames. As exemplified in FIGS. 7A-7F, a wide range of embodiments having different cross-sections can be provided according to the methods and materials disclosed herein.

The structural frame, where present in the mono-component composite or multi-component composite, can vary. Structural frames can take various forms including, but not limited to, stents, occlusion coils or frames, regenerative medicine scaffolds, structural reinforcements, pacing or monitoring leads, tissue anchors or tacks, biological stimulation devices, biomimetic implants, signal receivers or transmitters, orthopedic fixation devices or any other metallic, polymeric, ceramic or other therapeutic devices. Various stent types and stent constructions may be employed in the present disclosure, including, but not limited to, self-expanding stents and balloon expandable stents. In certain embodiments, the stents may be capable of radially contracting as well. Self-expanding stents include those that have a spring-like action which causes the stent to radially expand, or stents which expand due to the memory properties of the stent material for a particular configuration at a certain temperature.

The makeup of the structural frame, where present, can vary. In some embodiments, the structural frame is a metal structural frame, which can generally comprise any biocompatible metal. In certain embodiments, the metal structural frame can comprise stainless steel, platinum, gold, titanium, or a mixture thereof. In certain embodiments, the metal structural frame can comprise cobalt, chrome, or magnesium alloy. Nickel titanium alloy ("Nitinol") is one material which has the ability to perform well while both in spring-like mode, as well as in a memory mode based on temperature and thus may be useful in certain embodiments of the invention. In other embodiments, the structural frame can comprise another type of material, such as a ceramic.

The configuration of the structural frame (e.g., stent) may also be chosen from any suitable geometry. For example, wire stents can be fastened into a continuous helical pattern, with or without a wave-like feature or zig-zag in the wire, to form a radially deformable stent. Individual rings or circular members can be linked together by struts, sutures, welding, or interlacing or locking to form a single tubular stent. Individual rings or circular members may have no link and thus may serve as individual units in the composite that is provided upon the combination of such a frame with one or more layers of polymeric material according to the invention. In such cases, multiple ring segments are embedded and held in place by the composite material to comprise a single tubular composite device. Tubular prosthetic devices useful in the present invention also include those formed by etching or cutting a pattern from a tube. Such devices are often referred to as "slotted" devices (e.g., slotted stents). Furthermore, devices may be formed by etching a pattern into a material or mold and depositing device material in the pattern, such as by chemical vapor deposition or the like. As will be apparent based on the disclosure herein, there may be some limit on the configuration of a structural frame in order to achieve enhanced bonding between adjacent polymeric layers through the structural frame in certain embodiments.

It is noted that the examples provided herein and the embodiments illustrated in FIG. 7A-7F contain a structural frame; however, this is not necessary. In some embodiments, a 100% electrospun polymer-based device is provided. In other embodiments, a device is provided consisting only of a structural frame and electrospun polymeric layers. Composite devices comprising additional types of materials, however, are not intended to be excluded from the present disclosure. It is possible according to the present invention to incorporate various additional non-electrospun components into the mono-component prosthetic devices and multi-component prosthetic devices described herein. For example, such further components include, but are not limited to, melt-processable polymers, e.g., polyamides, polyurethanes, and the like (including, but not limited to, perfluoroalkoxy (PFA), fluorinated ethylene propylene (FEP), ethylene tetrafluoroethylene (ETFE), or tetrafluoroethylene hexafluoropropylene vinylidene fluoride (THV)) (which can provide a non-porous layer, e.g., as a self-sealing thermoplastic or elastomeric film); woven or nonwoven fabrics of natural or man-made fibers; plastic or ceramic membranes; metal, ceramic, or plastic meshes; expanded PTFE (ePTFE) layers as discussed for example in U.S. Patent Application Publication Nos. 2011/0030885 and 2011/0031656 to Anneaux et al., which are both incorporated herein by this reference in their entireties or combinations thereof.

Additionally, in some embodiments, the composite devices provided herein can comprise one or more bioactive agents. Examples of such bioactive agents that can be utilized in connection with the devices of the present disclosure include, but are not limited to: antibiotics, antifungals, and antivirals (such as erythromycin, tetracycline, aminoglycosides, cephalosporins, quinolones, penicillins, sulfonamides, ketoconazole, miconazole, acyclovir, ganciclovir, azidothymidine, and interferons); vitamins; anticonvulsants (such as phenytoin and valproic acid); antidepressants (such as amitriptyline and trazodone); antiparkinsonism drugs; cardiovascular agents (such as calcium channel blockers, antiarhythmics, and beta blockers); antineoplastics (such as cisplatin and methotrexate), corticosteroids (such as dexamethasone, hydrocortisone, prednisolone, and triamcinolone); NSAIDs (such as ibuprofen, salicylates, indomethacin, and piroxicam); hormones (such as progesterone, estrogen, and testosterone); growth factors; carbonic anhydrase inhibitors (such as acetazolamide); prostaglandins; antiangiogenic agents; neuroprotectants; neurotrophins; growth factors; cytokines; chemokines; cells (such as stem cells, primary cells, and genetically engineered cells); tissues; other agents known to those skilled in the art; and combinations thereof. Bioactive agents can, in some embodiments, be as described in U.S. application Ser. No. 13/272,412 to Ballard et al., filed Oct. 13, 2011, which is incorporated herein by this reference in its entirety. The amount of optional bioactive agent incorporated within the tubular composite devices can vary but is generally that amount sufficient to elicit a desired response in the patient in whom the device is to be implanted. In some embodiments, a bioactive agent can be incorporated within only one layer or within more than one layer of the composite prosthetic device. The properties and characteristics of the final composite prosthetic devices of the present disclosure are a compilation of the properties of the one or more espun polymer layers and any other optional material(s) contained within the composite device (e.g., the optional one or more additional espun polymeric layers and the optional structural frame). The final composite devices of the present disclosure can, in certain embodiments, be prepared with controlled fiber sizes and the mechanical properties of the device can be tailored so as to improve such features as bond strength between components (e.g., layers) of the device, elongation properties, and tensile strength. Moreover, different pore sizes of the layers can be targeted for different intended application. Advantageously, the individual layers exhibit little to no delamination, indicative of strong adhesion of layers to each other. The composite devices of the present disclosure can, in some embodiments, exhibit additional desirable characteristics of enhanced radial tensile strength, suture hole tearing resistance and enhanced axial tear resistance as compared with commercially available products.

The ability to tailor such properties of the composite device of the present disclosure can have implications in designing prosthetic devices for particular applications. Advantageously, the properties of individual layers of the composite device can be modified to tailor the overall properties of the composite device for a given application. For example, modifying the pore sizes and/or thicknesses of the polymeric layers can serve to enhance or inhibit cellular ingrowth or attachment. For example, the device interior surface, or ID surface (generally the fluid-, e.g., blood-contacting region) and the device exterior surface, or OD surface (which is generally the tissue-contacting region) may, in certain embodiments, have different effective pore sizes. In certain embodiments, it may be desirable to enhance cellular ingrowth and/or attachment on the exterior of a composite device, whereas it may be desirable to inhibit such activity on the interior of a composite device to allow fluid to freely pass therethrough. Thus, in some embodiments, a composite can comprise a layer having a large pore size on the exterior of the device to facilitate ingrowth and a layer having a smaller pore size on the interior of the device. In some embodiments, the inverse is desired (i.e., a composite with minimal to no ingrowth on the exterior and enhanced ingrowth on the interior), which can be achieved by providing a composite comprising a layer having a small pore size on the exterior of the device and a layer having a larger pore size on the interior of the device.

Electrospinning Process

Electrospun mats useful according to the present disclosure can be prepared by drawing material by electrical charge from a polymer solution, from a polymer suspension/dispersion, or from a polymer melt. The fibers thus produced are typically collected in a random fashion to produce nonwoven materials. Various specific techniques are known for the production of electrospun fibers and electrospun materials (e.g., mats and/or coverings).

Dispersion-spun layers (e.g., PTFE and other fluorinated polymers discussed herein) can be prepared, for example, according to the following procedure. A dispersion comprising the desired polymeric particles is provided or prepared. The solids content of PTFE resins is preferably between 50% to about 80% by weight, and more preferably between about 55% and about 65% by weight. In one specific embodiment, an exemplary commercially available PTFE dispersion, Daikin D 210 PTFE, is used, which comprises about 59-61 wt % PTFE solids (measured according to ASTM D 4441), 6.0-7.2% wt % surfactant, a pH at 25° C. of 8.5 to 10.5, a specific gravity of 1.50 to 1.53 and a Brookfield viscosity maximum of 35 cP. The properties of the PTFE (e.g., molecular weight, polydispersity index, particle size, particle size distribution) can vary. In some embodiments, the average particle size of the PTFE can be between about 0.05 µm and about 1 µm (for example, between about 0.1 µm and about 0.5 µm). In some embodiments, the average particle size is less than about 0.5 µm, less than about 0.4 µm, less than about 0.3 µm, or less than about 0.2 µm. For example, the average particle size in certain embodiments may be about 0.13 µm, about 0.16 µm, about 0.23 µm, or about 0.25 µm. The solvent can be any solvent suitable for creating a dispersion; suitable such solvents include, but are not limited to, aqueous solutions or alcohol solutions (e.g., methanol, ethanol, or isopropanol).

A fiberizing polymer is typically added to the dispersion to facilitate fiber formation and is generally removed following the espinning process. The fiberizing polymer (or polymers) are typically selected such that they have a high solubility in the solvent of the dispersion (e.g., where the dispersion comprises water, any water-soluble polymer can be used, including, but not limited to, poly(ethylene oxide)). The amount of fiberizing polymer present in the dispersion can vary; for example, in certain embodiments, the dispersion comprises about 1% to about 10% by weight of a fiberizing polymer, based on the total weight of the dispersion. In certain embodiments, the weight ratio of fiberizing polymer to PTFE varies. For example, the amount of fiberizing polymer can be about 3.0% to about 5.5% that of the PTFE in the dispersion by weight. The amount of fiberizing polymer required according to the present invention may vary depending on the chemical makeup of the polymer.

In preferable embodiments, the viscosity of the dispersion is within a certain desirable range to allow for the formation of uniform and consistent fibers therefrom (e.g., greater than about 50,000 cP, such as between about 50,000 cP and about 300,000 cP or between about 70,000 cP and about 150,000 cP, as measured with a Brookfield Viscometer. The desired viscosity of the dispersion may vary depending on whether a free surfaced-based apparatus or an orifice (needle)-based apparatus (which requires a somewhat higher viscosity) is used. In one embodiment, free surface electrospinning from a wire, a cylinder in a trough (i.e., open bath), spike, sharp edge, or similar geometry spinning electrode or the like is used. For the open bath unit, the ejection volume is dependent upon the viscosity of the dispersion, the conductivity of the dispersion, the surface tension of the dispersion, the distance from bath to target, and the voltage. These factors can also affect the thickness of the fabric and the fiber diameter. The charge source is preferably connected to the positive side of a precision DC power supply. The negative side of the power supply is preferably connected to the collection surface. Alternatively, the collection surface can be at ground. The polarity can be reversed but this is not preferred. Voltage is applied (e.g., typically from about 40,000 volts to about 120,000 volts (e.g., about 40,000 to about 80,000 volts) over a typical collection distance of about 100 to about 400 mm) to uniformly draw out the dispersion and attract it to a collection surface. In a free surface electrospinning apparatus, the collection surface/target can be placed, for example, above the cylinder in the dispersion trough or the dispersion-coated wire and is typically moved in at least one direction such that the entire surface or the desired portion thereof becomes uniformly covered with fibers.

In other embodiments, orifice or needle spinning is used. This method is similar to that described above; however, the polymeric dispersion passes through one, two, or several orifices and forms espun fibers and fabrics in this way. The voltage on the power supply is increased to the desired voltage (usually from about 2,000 to about 20,000 volts) to uniformly draw out the dispersion and attract it to the collection surface. The collection surface is preferably placed perpendicular to the orifice and is rotated such that the entire surface is uniformly covered, with the fibers drawn towards the collection surface.

General information related to processes for processing and electrostatic spinning from dispersion (e.g., of PTFE from aqueous and other dispersions) is provided, for example, in U.S. Pat. No. 4,323,525 to Bornat and U.S. Pat. No. 4,044,404 to Martin et al., which are incorporated herein by reference in their entireties. In certain embodiments, electrospinning of PTFE may be based at least in part, on the process described in detail in U.S. Patent Appl. Publ. Nos. 2010/0193999 to Anneaux et al. and 2012/0114722 to Ballard et al., which are both incorporated herein by reference in their entireties. Various parameters of the nanofiber production process can be modified to alter the properties of the resulting dispersion-spun (e.g., PTFE) material. For example, increasing the length of time generally increase the thickness of the espun material.

As described above, the composite devices described herein can, in some embodiments be multi-component composite devices comprising at least one solution-spun or melt-spun component. Solution electrospinning is generally known in the art and, in some embodiments, can be conducted in a similar way as the dispersion-based electrospinning described above. Similar to dispersion-based electrospinning, an electrical charge is used to draw polymeric fibers from the solution, which are deposited, generally in a random fashion, on a collection surface.

In solution-based electrospinning, the solvent in which the polymer is dissolved and the parameters required to produce fibrous mats via electrospinning can vary, depending upon the nature of the polymer. For example, where the polymer is PU, any solution in which the polymer is dissolvable (e.g., tetrahydrofuran (THF), dimethylformamide (DMF), dimethylacetamide (DMAc), and combinations thereof) can be used. In some embodiments, it may be useful to use a combination of solvents such that one solvent evaporates more quickly than the other as the fibers are produced. The concentration of polymer in the solution can vary, but is generally relatively low (e.g., less than about 25% by weight, less than about 10% by weight, such as between about 1% and about 10% by weight).

Parameters such as makeup of the solution (e.g., the solvent, the composition and molecular weight of the polymer used, any additives, the concentration of the polymer in the solution, the solubility of the polymer in the solvent, etc.), the charge applied to the solution, the time period of electrospinning, etc. can impact the fibrous mat thus produced. Exemplary methods are described, for example, in U.S. Pat. Nos. 1,975,504; 2,160,962; and U.S. Pat. No. 2,187,306, all to Formhals; Demi et al., *Polymer* 43: 3303-3309 (2002); Greiner et al., *Angew. Chem. Int. Ed Engl.* 46(30: 5670-5703 (2007), and Bhardwaj et al., *Biotech. Adv.* 28(3): 325-327, which are all incorporated herein by reference in their entireties. These and other methods for the preparation of electrospun mats from solution can be used according to the present disclosure.

Melt electrospinning is similar to dispersion and solution electrospinning, but involves electrospinning fibers from melted polymer. Any polymer that can be placed in melt form has the potential to be electrospun by this method. A melted polymer sample to be spun can be prepared, for example, by heating from resistance heating, circulating fluids, air heating, or lasers. The temperature at which melt spinning is conducted will vary depending upon the melting point of the polymer or polymers used.

In all types of electrospinning (i.e., solution-based, dispersion-based, and melt-based electrospinning, the collection surface onto which the spun fibers are deposited can vary and can be dependent upon the type of electrospinning setup used. In certain embodiments, the collection surface is a sheet, the surface of which can be, e.g., any metal or polymeric material, with stainless steel being a particularly preferred material. In other embodiments, the collection surface is a tubular prosthetic device (e.g., in the form of a stent, stent-graft, or graft). In certain embodiments, the collection surface is a drum (i.e., a cylinder around which a collection sheet can be wrapped), which may be rotated during collection to generate a tubular structure. The tubular structure can be cut along the length of the tube to provide a sheet. In certain embodiments, the collection surface is a rod or tube (i.e., a mandrel around which a collection sheet may be wrapped or on which the fibers may be collected directly) which may be rotated during the collection to generate a tubular structure. Such a tubular structure can, in certain embodiments, be directly used in its tubular form.

Electrospun materials produced via solution and melt spinning are generally sufficient for manipulation immediately following production and generally do not require any further treatment to provide the desired fiber characteristics. However, in dispersion-based electrospinning, the polymeric (e.g., PTFE) mat/sheet, tube, or covered device is generally somewhat fragile and typically must be heated and/or sintered to provide a sufficiently strong and durable material for use as a component of a prosthetic device according to the invention. Heating generally serves to dry the material, volatilize and remove the fiberizing polymer, and/or to sinter the PTFE particles (e.g., by fusion of individual PTFE particles to produce a nonwoven, PTFE-based material). The sintering of the material generally results in the formation of a stronger, more durable material. The level of sintering can vary. During heating, the material can be monitored to evaluate the sintering level by various methods (e.g., calorimetry and/or visual inspection).

The material can be heated in place (i.e., by placing the entire collection surface in an oven) or by removing the electrospun material from the collection surface prior to heating and placing the free electrospun material in an oven. As will be described in greater detail herein, the PTFE sheet or tube or PTFE-covered device can be heated and sintered alone, or in certain embodiments, it may be combined with other components of the composite device prior to heating. Thus, the heating and sintering can occur at any stage of the process of assembly of the composite prosthetic device. It is noted that the components of the composite structure must be considered to ensure that the other components can withstand the conditions required to sinter the PTFE (or other dispersion-spun polymer).

The time and temperature at which the material is heated can vary. For example, in typical embodiments, to sinter a PTFE material (e.g., sheet, tube, or covered device), the temperature of the oven is between about 250° C. and about 800° C., such as between about 300° C. and about 500° C. (e.g., between about 350° C. and about 485° C.). The PTFE (or other dispersion-spun polymeric material) is generally exposed for a period of time such that any remaining water is evaporated and the fiberizing polymer undergoes decomposition and subsequent elimination of the residual material. It is noted that, in some embodiments, PTFE can be sintered in combination with one or more additional materials. This advantageously is only conducted where the characteristics of the one or more additional materials are such that the material or materials can withstand the high temperatures required for PTFE heating/sintering). It is important to distinguish sintering and heating steps. Sintering is generally used only where unsintered espun PTFE (or similar dispersion-espun polymer) is present and must be conducted in the absence of other material that may be negatively affected by the high temperatures required for sintering.

The time for which a dispersion-espun material is heated to sinter the material may depend, in part, on the temperature of the oven. In some embodiments, the material is sintered for a period of about an hour or less, about 30 minutes or less, about 20 minutes or less, about 15 minutes or less, or about 10 minutes or less. For example, in certain embodiments, the sintering is conducted for a time of between about 2 and about 30 minutes, preferably between about 5 and about 20 minutes. It is noted that more time may be required for sintering at lower temperature and less time may be required for sintering at a higher temperature. The time required for drying and sintering can also depend on the thickness of the material, with thicker materials requiring more time to dry and/or sinter.

The drying, volatilizing, and sintering of a dispersion-spun material can occur simultaneously or in a series of steps. While not intended to be limited by any theory, it is believed that some drying (i.e., removal of the solvent) may occur upon completion of electrospinning. It is further believed that some small degree of fiber rearrangement may occur at this point. Then when the material is heated, preferably, the majority of the solvent and the fiberizing polymer (e.g., greater than about 80%, preferably greater than about 90% or 95%, and most preferably greater than about 98 or 99%) is removed from the PTFE material. It is understood that espun fabric generally undergoes shrinkage upon heating/sintering. While not limited to any theory, the shrinkage is believed to occur in two steps: the initial drying and fiber rearrangement following the electrospinning process, and the removal of solvent and fiberizing polymer by heating/sintering.

Preparation and Use of Composite Prosthetic Devices

There are various means for producing the components of the composite prosthetic devices described herein and for combining the components to form composite devices, which will be described in further detail herein. In general, the method comprises assembling the one or more layers to be incorporated within the composite and applying heat and/or pressure to provide a composite prosthetic device.

Depending on the chemical makeup of the components and the physical form of the one or more electrospun materials (i.e., whether in a sheet form, tubular form, or as a covering directly spun onto a device) to be incorporated within the composite device, the means by which the final structure is assembled can vary.

In certain embodiments, an electrospun polymer sheet or tube is produced independently and then combined with the one or more additional layers to form a composite structure. The polymer sheet can be a single polymer sheet (e.g., a sintered PTFE mat, a PU mat, a PDMS mat, etc.). In other embodiments, a multi-layered espun polymer sheet ("combination sheet") can be provided. For example, in certain embodiments, an espun PTFE mat is produced and sintered. Another polymer is then directly electrospun onto the sintered espun PTFE mat, producing a two-layered mat of electrospun polymer. For example, in the preparation of mono-component composites, one espun PTFE mat can be prepared and another espun PTFE layer can be deposited directly thereon. In the preparation of multi-component composites, one espun PTFE mat can be prepared and another type of polymer can be directly electrospun thereon (e.g., PU or PDMS). Such combination mats can be provided with varying combinations of espun polymeric layers and with varying numbers of such layers.

A mat (a single electrospun mat or a combination sheet) can, in certain embodiments, be "laminated" onto another material (e.g., onto a polymeric tube, a structural frame, or onto a covering thereon), e.g., by wrapping the mat around the other material. This process generally involves layering or wrapping the espun mat or mats directly onto or around the material to be covered, giving a prosthetic composite device precursor, and applying heat and/or pressure thereto to provide a prosthetic composite device. The layering or wrapping can be performed such that the sheet/layer is wrapped one time around a construct or multiple times around the construct (e.g., two times, three times, four times, or more times). In some embodiments, (i.e., where a single electrospun mat is wrapped), the number of wrappings of each sheet can affect the thickness of that layer of the final composite. For example, a device wherein a given electrospun mat is wrapped twice around a construct will give a thicker layer of that electrospun material in the final device than in a device wherein that electrospun mat is wrapped only once around the construct. The overall wall thickness of a device having a greater number of wrappings will thus be thicker as well. Where a combination sheet is used, the number of wraps will alter the number of layers of the two (or more) components comprising the combination sheet. For example, a combination sheet wrapped once around a construct adds two additional layers (i.e., having different compositions from the two polymers comprising the combination sheet). A combination sheet wrapped twice around a construct adds four additional layers (i.e., alternating the two compositions from the two polymers comprising the combination sheet). FIGS. 7A and 7B and FIGS. 7D and 7E are comparable to one another except that the number of wrappings of the outer two components are different, as will be described in greater detail below.

Although in certain embodiments, the wrapping methods described above are useful in preparing mono-component and multi-component prosthetic devices according to the present disclosure, the disclosure is not intended to be limited to such methods of preparation. In some embodiments, a polymer is directly spun onto another component of the composite prosthetic device. For example, electrospinning can be conducted such that a polymer covering is directly spun onto a construct (e.g., a polymeric tube or a structural frame, such as a stent). In certain embodiments, two or more methods can be combined (e.g., a covering can be applied to a structural frame by directly electrospinning the covering thereon and the resulting device can be subsequently wrapped with a second covering and treated as described herein or a covering can be applied to a structural frame by wrapping and a second covering can be applied to the covered structural frame by directly electrospinning the second covering thereon).

As noted above, the composite prosthetic devices of the present disclosure generally incorporate at least one tie layer, which can be incorporated within the device precursor as an unsintered dispersion-spun layer (which is subsequently sintered prior to use of the device) or which can be a solution-spun or melt-spun layer (which does not require sintering prior to use of the device). The tie layer can be applied using any of the methods described herein. The tie layer can serve as a "glue" to bind to another layer and preferably can be used to bind multiple layers together. In embodiments wherein a structural frame is present, the tie layer can penetrate the open spaces in the structural frame and bond to the material on the other side of the structural frame (e.g., where the tie layer is provided on the outer surface of the structural frame, it can penetrate the frame and bond to the material comprising the inner diameter surface of the structural frame which may, in some embodiments, be a porous electrospun polymeric layer). Thus, in certain embodiments, the tie layer may serve to bond and/or connect the material on the inner diameter surface of the composite device to the material on the outer diameter surface of the composite device. In some embodiments, a significant advantage to the presence of such a tie layer is that it can serve to create a better bond and/or seal between various layers of the composite device following the application of heat and/or pressure to the composite device precursor. This bonding can be characterized, for example, by an enhanced peel strength between certain layers.

For example, in certain embodiments, the preparation of composite devices of the present disclosure involves the incorporation of an unsintered PTFE tie layer. The stage at which any unsintered PTFE present in the composite device is sintered must be such that no material is present that will be negatively affected by the temperatures required for the sintering of the PTFE. For example, where PU is to be included in a multi-component composite device, any unsintered PTFE layer(s) applied to the device should be sintered prior to the application of the PU to avoid destroying the porous PU layer(s) during the sintering of the PTFE layer(s). For this reason, it is noted that an unsintered PTFE layer is generally useful as a tie layer in composites only where the adjacent layers of the device precursor comprise PTFE or another, similar polymer (and not in composites wherein a PU or other, similar polymer is adjacent to the unsintered PTFE).

In certain embodiments, the preparation of composite devices of the present disclosure involves the incorporation of a solution-spun tie layer (e.g., including, but not limited to, PU or PDMS). Such tie layers, which do not require sintering prior to use of the composite device, can be advantageous as the processing of the device does not require the structural frame, where present, to be exposed to the high temperatures required for sintering (as required for, e.g., a PTFE tie layer). In certain embodiment, avoidance of such high temperatures can serve to keep the mechanical properties and integrity of the device more intact.

The amounts and relative amounts of material in the layers of the composite prosthetic devices described herein can vary. It is noted that, with regard to the tie layer, in embodiments wherein a structural frame is present, the wire/strut diameter, spacing between the wires/struts struts, and/or the processing conditions may impact the amount of material required to ensure sufficient bonding of the tie layer to other layers and/or to the structural frame. For example, large wire or strut diameters or thicknesses may need more of the tie-layer espun polymer material as compared to smaller wire or strut diameters (which can be provided, e.g., by using a thicker espun sheet and/or by wrapping a sheet more times around the device). It is noted that a structural frame with minimal spacing between the wire or strut lattice may not perform as well due to minimal inner diameter and outer diameter contact, resulting in a poorly secured and embedded structural frame. However, even structural frames with minimal spacing between the wire or strut lattice can perform well if enough tie layer espun polymer material is used and enough heat and/or pressure is applied to ensure that the tie layer espun polymer can penetrate the open spaces in the lattice. Generally, there is a certain amount of tie layer material that must be applied to the structural frame, a certain amount of processing (e.g., temperature and/or pressure) that must be applied to the structural frame, there must be a sufficient amount of open space in the frame to ensure that the frame is not "floating" within the composite and is adequately affixed onto or within the other layers of the composite, and the tie layer material must have sufficient properties (e.g., flowability and/or tackiness) to enable it to effectively penetrate the open spaces of the structural frame.

Following the wrapping or other means of applying one or more layers (including one or more tie layers) to produce a mono-component or multi-component composite prosthetic device precursor, the device precursor is subjected to heat and/or pressure. The application of heat and/or pressure to the precursors as intended herein generally results in some degree of fusion and/or merging of the various layers of the composite device precursor (e.g., via the tie layer penetrating through the open spaces in a structural frame and/or penetrating the pores of at least one of the adjacent layers). In some embodiments, the application of heat and/or pressure can also ensure that the inner diameter surface of a composite device is bonded to the outer diameter surface of the composite device. In embodiments wherein a structural frame is present, application of heat and/or pressure can advantageously seal the frame within the composite device so that there is no delamination and/or so that the frame is completely covered by one or more polymeric layers. In certain embodiments, application of heat and/or pressure can result in a decrease in effective pore size of the individual layers and/or composite as a whole and/or can result in a decrease in individual layer thickness and/or wall thickness of the composite as a whole.

The amount of heat and the method by which the heat is applied to the device precursor can also vary. In certain embodiments, heat can be applied by heating the device precursor in various types of chambers (e.g., heating vessel or clamshell) or by heating the device in an oven. Where a multi-component prosthetic device precursor is provided, heat applied at this stage is typically significantly lower than the heat required to sinter the dispersion-spun component or components (e.g., PTFE). The temperature applied can vary depending on the makeup of the device precursor, as discussed in greater detail below. Thus, in certain embodiments, the one or more dispersion-spun components are present in sintered form when the heat and/or pressure is applied to the multi-component device precursor. Where a mono-component prosthetic device precursor is provided, having one or more unsintered, dispersion-spun layers therein, the heating step can include sintering. In such embodiments, heat and/or pressure is applied to the device precursor to cause the unsintered dispersion-spun tie layer to penetrate the pores of one or both of the adjacent layers (and, optionally, to penetrate through the open pores of the structural frame, where present) and the heat applied can advantageously be sufficient to sinter the one or more unsintered dispersion-spun component. Although, in such embodiments, the heat and/or pressure required to ensure penetration of one or more layers as described herein may be insufficient to sinter the unsintered dispersion-spun component, it is advantageous in some embodiments to apply heat and/or pressure and sinter simultaneously, i.e., by ensuring that the heat applied is sufficient to sinter the dispersion-spun component.

In some embodiments, pressure can be applied by using a flat press, constricting wrap, and/or mechanical nip roller. In certain embodiments, physical pressure is applied to the device precursor by wrapping the construct with a constricting wrap and applying pressure, either directly or indirectly. In some embodiments, the constricting wrap is maintained on the covered construct and the entire device precursor, including the constricting wrap, is heated; subsequently, the constriction wrap is removed to provide a compressed composite device. In some embodiments, pressure can be applied to the device precursor in a pressure vessel. Pressure vessels of varying design and size can be useful according to the methods provided herein. In some embodiments, the pressure vessel can be a heated pressure vessel, allowing heat and pressure to be applied to a device precursor simultaneously. The pressure rating of the vessel can vary, so long as sufficient pressure may be applied to the device precursor to allow the tie layer to penetrate through the open spaces in a structural frame and/or to penetrate the pores of at least one of the adjacent layers. Exemplary pressure vessels include, but are not limited to, Non-Stirred Pressure Vessels from Parr Instrument Company (Moline, Ill.). Other means for the application of pressure are intended to be encompassed herein as well. Due to the porosity of the composite device precursors described herein, it may be necessary, in certain embodiments, to enclose the device precursor in a non-porous material prior to introducing it into the chamber. It is to be understood that selection of the non-porous material must be based on the conditions to which the device precursor will be subjected in the chamber. For example, the non-porous material must be capable of withstanding the elevated pressure and/or temperature conditions within the chamber without negatively impacting the enclosed composite device precursor and/or device.

In embodiments wherein both heat and pressure are applied to the device precursor, it is not necessary for the heat and pressure to be applied simultaneously, but in some embodiments, they may be applied simultaneously (e.g., in a heated pressure vessel). Further, it is noted that the application of pressure and/or heat may be conducted at various stages of construction of the composite prosthetic device. In some embodiments, pressure is applied, followed by the application of pressure and heat. In some embodiments, the entire device is assembled and pressure and/or heat are applied to provide the final device. In other embodiments, the application of pressure and/or heat can be conducted at one or more stages during the assembly process.

The amount of heat and/or pressure advantageously applied to prepare the composite device precursor can depend on the makeup of the layers of the device. In specific embodiments, the applied pressure is between about 500 and about 1500 PSI and the temperature is at least about 50° C. or at least about 100° C. (e.g., between about 75° C. and about 400° C. or between about 100° C. and about 300° C.). It is understood that the time and temperature are related, i.e., increasing the temperature at which the device precursor is treated may allow for a decrease in the pressure applied (particularly where the temperature and pressure are applied simultaneously). The temperature can also depend on the makeup of the composite device precursor. For example, where at least one component of the precursor comprises unsintered PTFE, the composite device is preferably heated at a temperature sufficient to sinter the unsintered PTFE (e.g., about 385° C.). Where no unsintered espun PTFE is present in the device (e.g., where the tie layer comprises PU or PDMS), the temperature applied is advantageously significant lower (e.g., between about 100° C. and about 200° C.).

The time at which heat and/or pressure is applied can also vary; generally, the device precursor must be exposed to the heat and/or pressure for a sufficient period of time to ensure that the tie layer can penetrate through the open spaces in a structural frame and/or can penetrate the pores of at least one of the adjacent polymeric layers (e.g., at least about 3 minutes, at least about 5 minutes, or at least about 7 minutes, including between about 3 and about 20 minutes, between about 5 and about 15 minutes, between about 5 and about 10 minutes, and between about 5 and about 7 minutes). Although such times are noted to be useful, it is understood that in some embodiments, the composite device can be heated for lesser or more amounts of time. Generally, the heat and/or pressure should be applied for a period of time sufficient for bonding. The time is also related to the heat and/or pressure, such that in some embodiments, treatment of the device precursor at a higher temperature and/or pressure may require less time than treating that same device precursor at a lower temperature and/or pressure. It is understood, however, that there is some minimum temperature and/or pressure that will be required to ensure the device exhibits penetration of the tie layer through the open spaces in a structural frame and/or to ensure penetration of the tie layers into the pores of at least one of the adjacent layers (e.g., in certain embodiments, ensuring bonding between the inner diameter surface of the composite device and the outer diameter surface of the device).

In some embodiments, the melt flow characteristics of a tie layer polymer may affect the choice of heat and/or pressure to be applied. For example, a tie layer comprising a polymer with a higher melt flow rate may require less heat and/or pressure to ensure that the tie layer effectively penetrate the pores of at least one of the adjacent layers, whereas a polymer with a tie layer comprising a lower melt flow rate may require more. Further, the presence of a structural frame may impact the amount of heat and/or pressure to be applied to the device precursor. In some embodiments, greater heat and/or pressure may be required to ensure that the tie layer can penetrate through the open spaces in the frame.

Additionally, a composite device comprising a structural frame with a thick wire or strut may not be prepared in the same way as a device comprising a structural frame with a thin wire or strut. For example, in some embodiments, a frame with a thick wire or strut or a frame with narrow spaced wires or struts may require more electrospun polymeric material (e.g., a thicker covering), may require the use of an electrospun polymeric material having a greater ability to flow and penetrate the open spaces (e.g., a polymer having a higher melt flow rate), and/or may require greater heating and/or pressure applied thereto to ensure that the covering can penetrate the open spaces within the frame. The spacing between wires or struts of a structural frame may similarly affect the materials and parameters of the methods used to form a composite device comprising the frame. For example, in some embodiments, where the structural frame has widely-spaced wires or struts (e.g., with amplitudes spaced relatively far apart and/or having fewer wires or struts), less heat and/or pressure may be required than for a comparable embodiment wherein the structural frame closely spaced wires or struts (e.g., with amplitudes closer together and/or having more wires or struts).

In embodiments wherein a thermoset polymer is employed (e.g., as a tie layer) in the composite prosthetic device precursor, the thermoset polymer is advantageously heat-cured during the application of heat and/or pressure as described above. In some embodiments, this curing requires a higher temperature than those noted above, e.g., at least about 200° C. In some embodiments, a thermoset polymer is employed that is cured through radiation. Advantageously, in embodiments wherein a thermoset polymer is used, it is not cured until during or after the heat and/or pressure treatment described above, such that it can flow into the pores of one or more adjacent layers in uncured form and subsequently be cured to provide a composite prosthetic device.

The layered approach to preparing the composite devices described herein provides the ability to tailor devices for particular applications. Tailoring as used herein refers to the ability to produce and use various materials with various properties. In some embodiments, tailoring relates to the process conditions used in espinning; by varying the parameters of the method, polymeric sheets, tubes, or covered constructs having different physical properties can be obtained. For example, where a thicker polymeric mat/tube (or a thicker covering directly spun onto a construct) is desired, the espinning process can be conducted for a longer period of time to deposit more material. As another example, where a polymeric mat with smaller pore size is desired, a thicker mat can be prepared, which typically results in a decreased pore size. In some embodiments, a smaller pore size can be obtained by decreasing the targeted fiber diameter. In some embodiments, tailoring relates to the method of assembly of the composite device. For example, where a thicker polymeric layer within the device is desired, a given polymeric mat can be wrapped around the composite device precursor a greater number of times. Thus, tailoring the properties of a given layer of the composite device can be done in various ways, relating to the production of the espun layer and/or the application of the espun layer to the composite device. In further embodiments, where a device having one or more impermeable portions is desired, a thermoplastic polymeric film may be incorporated within the composite device.

Further, as noted above, various additives, e.g., bioactive agents, can be included in one or more of the layers of the device. Such optional bioactive agents can be incorporated within composite devices in a variety of ways. For example, in some embodiments, the one or more bioactive agents can be directly incorporated into the fibrous mats by including them in a dispersion, solution, or melt that is espun, or the one or more bioactive agents can be incorporated into a layer or into the composite device after the fibers are prepared, e.g., by applying the bioactive agents, e.g., in solution form, onto/into the layer or device. Certain exemplary means for the incorporation of bioactive agents are described in U.S. application Ser. No. 13/272,412 to Ballard et al., filed Oct. 13, 2011, which is incorporated herein by this reference in its entirety. Although the referenced application is directed to the incorporation of antimicrobial agents, the antimicrobial agent could be replaced with the desired bioactive agent in the methods described herein.

The properties and characteristics of the final composite prosthetic device produced may be impacted by the application of heat and/or pressure. For example, the degree of heating (i.e., time and temperature), the amount of pressure applied, and the method by which the pressure is applied may affect the overall quality of the final composite. If there is not enough heat and/or pressure, poor bonding and delamination may occur, resulting in weak adhesion of the layers to each other. Additionally, without sufficient heat and/or pressure, some portion of the structural frame, where present, may be exposed (i.e., uncovered), which in certain embodiments is not desirable. Further, without sufficient heat and/or pressure, the structural frame, where present, may move within the composite device, which is typically undesirable.

The application of heat and/or pressure can have varying impacts on the composite prosthetic device. Generally, the application of heat and/or pressure results in some degree of fusion and/or merging of the various layers of the composite device. Advantageously, heat and/or pressure can serve to aid in the penetration of the material comprising the tie layer of the composite into the pores of one or both of the layers adjacent thereto. Where a structural frame is present, the heat and/or pressure can, in some embodiments, cause the tie layer to penetrate the open spaces in the frame. The heat and/or pressure is thus preferably such that the tie layer of the prosthetic device precursor is moldable or flows to some extent into the pores of adjacent layers (and, optionally, through the open spaces of a structural frame, where present). Where the tie layer of the composite device precursor comprises an unsintered, dispersion-spun fibrous mat (e.g., PTFE), additional heating is generally required to sinter the material. However, where the tie layer of the composite device precursor comprises a solution-spun material (e.g., PU or PDMS), such high temperatures are not required to provide the final product.

Use of a tie layer as described above (for example, in the form of an unsintered dispersion electrospun fibrous layer (e.g., PTFE) or a solution-spun fibrous layer (e.g., PU or PDMS)) between two or more other layers (and optionally through the open spaces of a structural frame) can provide significantly increased bonding between those layers following the application of heat and/or pressure (and, optionally, sintering, in the case of PTFE). This is especially noted in embodiments incorporating a tie layer adjacent to a structural frame, where the tie layer can bond to an additional polymeric layer (of various types) through the structural frame, in some embodiments, encapsulating the structural frame within the device. For example, a tie layer can, in certain embodiments, bond through a structural frame to a porous electrospun polymeric layer comprising the internal diameter surface covering of the composite device. The tie layer can also, in some embodiments, bond to an additional porous electrospun layer adjacent thereto, e.g., by penetrating the pores thereof. The composite devices described herein can, in certain embodiments, exhibit greater peel strengths between adjacent layers, which can result in enhanced performance of the resulting composite.

In certain embodiments, the application of heat and/or pressure to the composite prosthetic device precursor can result in a decrease in effective pore size of the walls of the device and/or can result in a decrease in the overall wall thickness of the device. In certain embodiments, the heat and/or pressure applied to the device precursor may impact the pore size and/or the thickness of one or more individual espun layers. An increase in pressure and/or temperature may be associated with a decrease in pore size and/or a decrease in the layer thickness. For example, a PU or other meltable polymer would be expected to flow to some extent upon the application of heat and/or pressure, thus reducing the effective pore size of the PU layer relative to the PU layer prior to the application of heat and/or pressure. However, polymers electrospun from solution (e.g., PU and PDMS), when incorporated within the composite structures by any of the means described herein, unexpectedly can exhibit some degree of porosity, even after the application of heat and/or pressure to ensure sufficient fusion between the layers of the final device. The effective pore sizes of certain layers can thus be controlled to some extent by both electrospinning conditions used to prepare the electrospun layer and by the treatment to which the layers are subjected within the composite device. In some embodiments, the effective pore size of the composite as a whole may not be reflective of the combination of effective pore sizes of the individual layers. Consequently, in some embodiments, the methods described herein provide devices incorporating thermoplastic polymers or thermoset polymers which exhibit some overall degree of porosity.

In some embodiments, varying the materials as well as the temperature and/or pressure at which the device is processed can provide devices exhibiting varying degrees of porosity, as evidenced by the ability to obtain effective pore size measurements of the device as a whole. As, in many embodiments, it is desirable to maintain pores in the final device, the materials and methods can be selected so as to ensure that porosity is maintained. The retention of some degree of porosity in an electrospun mat can be impacted, for example, by the melting point of the polymer and/or by the melt flow viscosity. Various parameters can affect these parameters including, but not limited to, the molecular weight of the polymer and the degree of branching within the polymer backbone. Consequently, a wide range of polymers can be tailored and optimized for use according to the present invention by varying these and other parameters and/or by blending two or more different types of polymers.

Exemplary preparation methods for certain composite prosthetic devices according to the present disclosure are further described and exemplified below. It is noted that these categories are not intended to be exclusive. In other words, two composite devices can, in certain embodiments, be separately prepared and combined. Accordingly, in some embodiments, two composites devices or components thereof can be separately prepared; subsequently, one composite can be wrapped around or inserted into another composite, and pressure and/or heat can be applied the entire combined composite structure to form a single composite prosthetic device. As another example, a polymer-based composite can be combined with a composite prosthetic device including a structural frame, e.g., by separately preparing the two device types and wrapping the polymer-based composite around the composite prosthetic device including a structural frame or inserting it into the inner diameter of the composite prosthetic device including a structural frame. Again, heat and/or pressure can then be applied to the entire structure to form a single composite prosthetic device. All combinations, as well as singular composite prosthetic devices as described herein are intended to be encompassed by the present disclosure.

Certain exemplary composite devices of the present disclosure and representative methods for preparing each are provided in FIGS. 7-11. These are only exemplary constructions and exemplary means for preparing such constructions. These schematics provided in the figures and described herein are presented only to give exemplary means by which the principles described herein can be applied to certain specific components (to generate the representative constructs illustrated in FIGS. 7A-7F).

Figure 8:
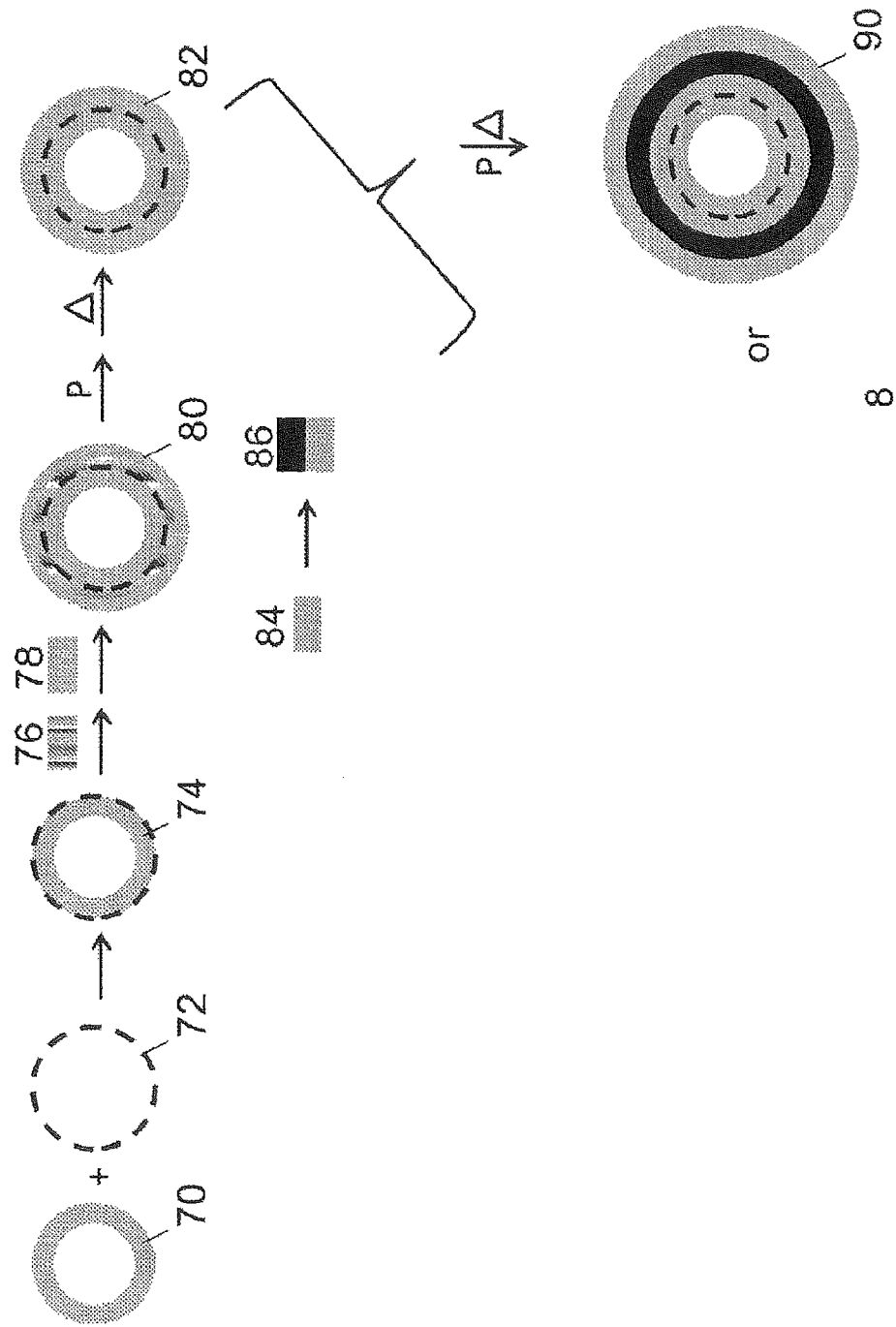
FIG. 8 is a schematic illustrating one exemplary process for the preparation of the exemplary composite devices of FIG. 7A and/or FIG. 7B.

FIG. 8 illustrates an exemplary preparation of the composite devices illustrated in FIGS. 7A and 7B. Briefly, an electrospun PTFE mat is prepared, sintered, and wrapped, e.g., around a hypotube, to form a tubular structure 70. A structural frame 72 is applied around structure 70, giving a frame-containing structure 74. An unsintered mat of espun PTFE 76 is wrapped around the structural frame (e.g., to serve as a tie layer) and a sintered espun PTFE mat 78 is wrapped around unsintered mat 76. Pressure and heat are applied to the resulting composite device precursor 80, sufficient to sinter the unsintered PTFE of tie layer 76, giving a mono-component device 82.

Independently, an electrospun PTFE sheet 84 is prepared and sintered; a combination PU/PTFE sheet 86 is prepared by electrospinning PU directly onto sheet 84. The combination sheet is wrapped around mono-component construct 82, with the PU layer laid directly against the outer surface of construct 82. The entire device precursor is then simultaneously subjected to pressure and heat. The multi-component cross-section on the left (88) depicts the result of the above process wherein the combination sheet is wrapped twice around the construct and the multi-component cross-section on the right (90) depicts the result of the above process wherein the combination sheet is wrapped once around the construct.

As such, in one embodiment, the present disclosure provides a method for producing a composite prosthetic device comprising: applying a structural frame over a porous electrospun poly(tetrafluoroethylene) tubular structure; wrapping an unsintered poly(tetrafluoroethylene) mat around the structural frame (one or more times); wrapping a sintered poly(tetrafluoroethylene) mat around the unsintered poly(tetrafluoroethylene) mat (one or more times); and heating the resulting construct to sinter the unsintered poly (tetrafluoroethylene). In certain embodiments, such a method can further comprise preparing a combination electrospun mat by electrospinning a different polymer onto a sintered poly(tetrafluoroethylene) mat; wrapping the combination electrospun mat around the construct (one or more times, with the different polymer surface of the mat in contact with the construct) to give a precursor; and applying heat and pressure to provide a composite prosthetic device.

Figure 9:
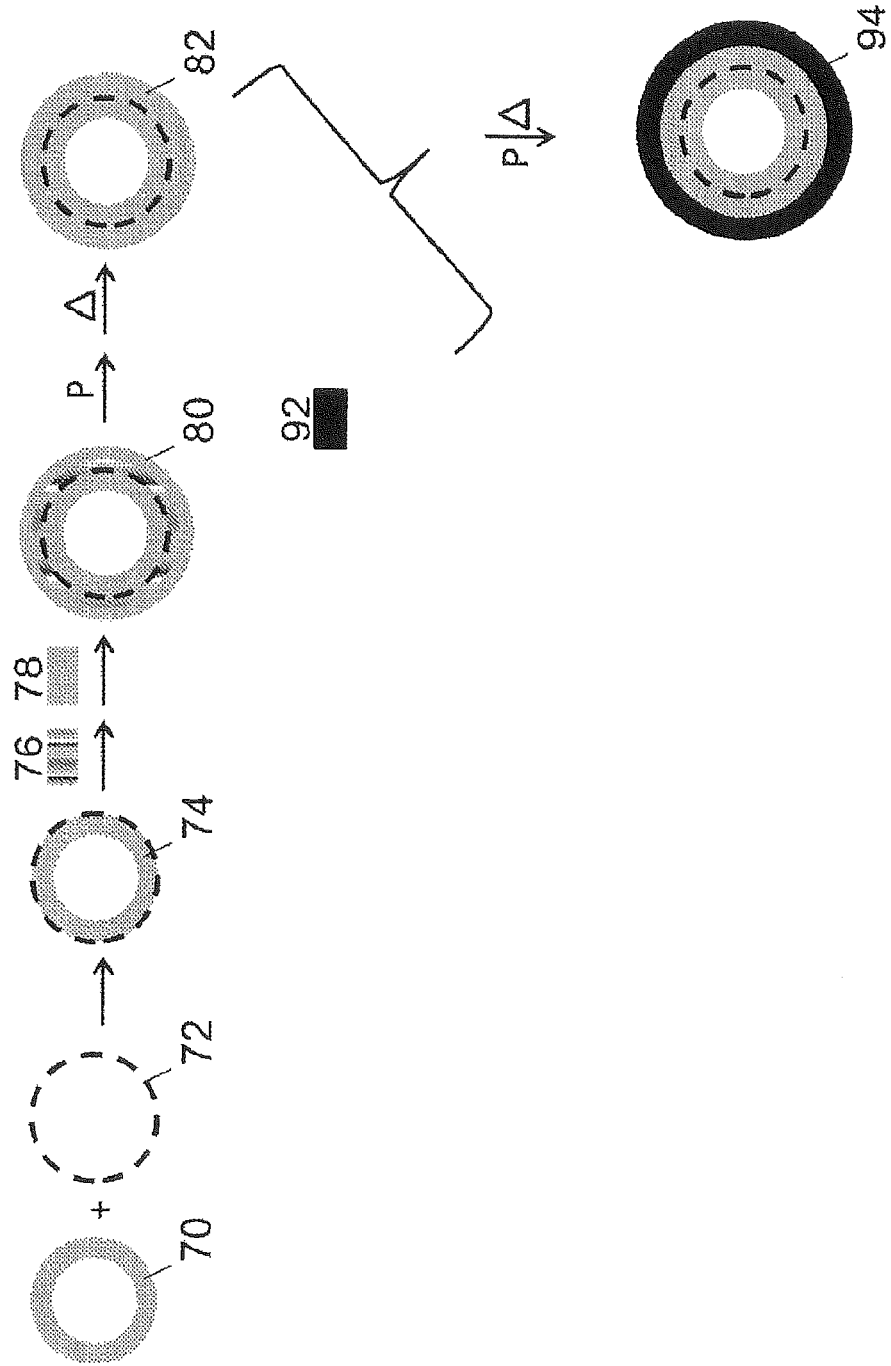
FIG. 9 is a schematic illustrating one exemplary process for the preparation of the exemplary composite device of FIG. 7C.

FIG. 9 illustrates an exemplary preparation of the composite device illustrated in FIG. 7C. The method is initially identical to that described above with regard to the method illustrated in FIG. 8. However, a single PU sheet 92 is independently prepared and wrapped around mono-component construct 82, rather than the combination sheet depicted in FIG. 8. The entire device precursor is then subjected to pressure and heat to give a multi-component composite device 94.

As such, in one embodiment, the present disclosure provides a method for producing a composite prosthetic device comprising: applying a structural frame over a porous electrospun poly(tetrafluoroethylene) tubular structure; wrapping an unsintered poly(tetrafluoroethylene) mat around the structural frame (one or more times); wrapping a sintered poly(tetrafluoroethylene) mat around the unsintered poly(tetrafluoroethylene) mat (one or more times); heating the resulting construct to sinter the unsintered poly(tetrafluoroethylene); wrapping an electrospun mat comprising a different polymer around the construct (one or more times) to give a precursor; and applying heat and pressure to provide a composite prosthetic device.

Figure 10:
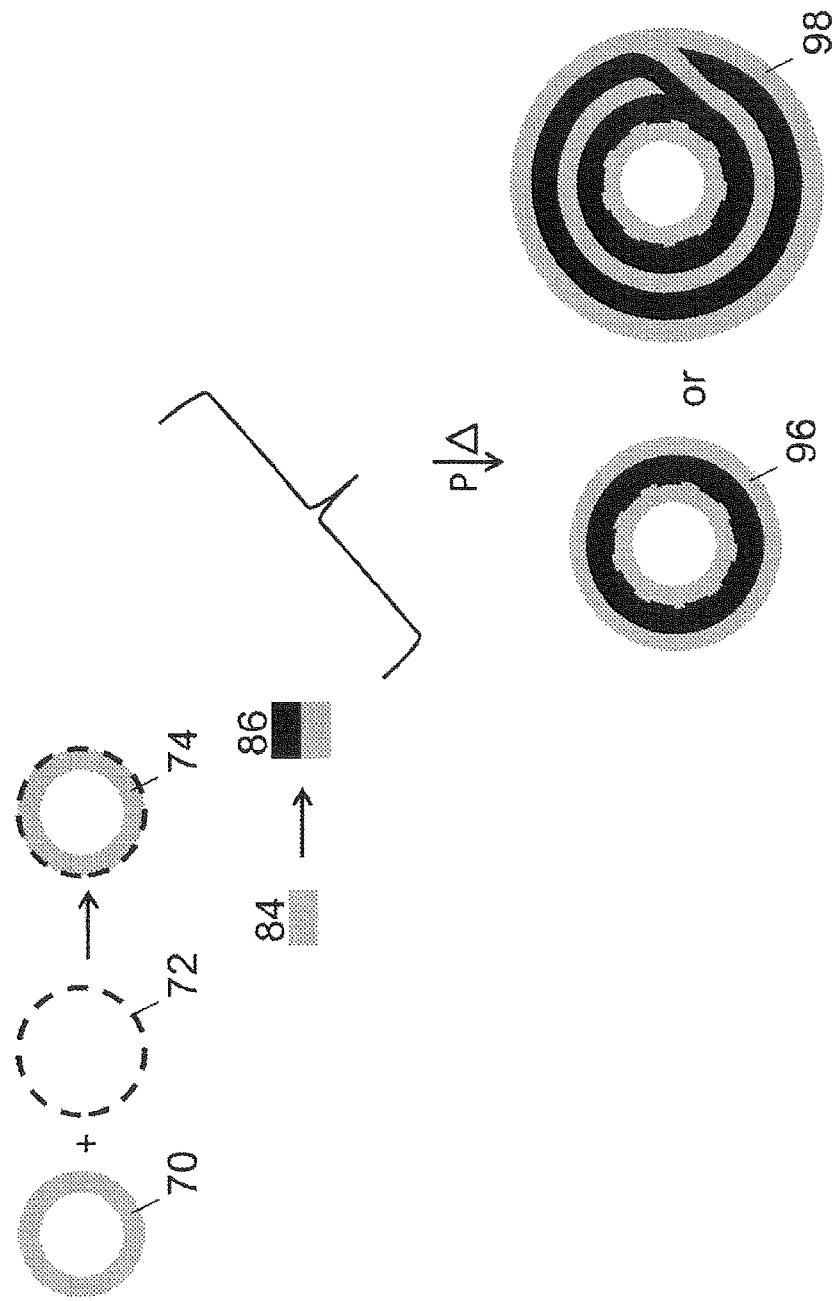
FIG. 10 is a schematic illustrating one exemplary process for the preparation of the exemplary composite devices of FIGS. 7D and 7E.

FIG. 10 illustrates an exemplary preparation of the composite device illustrated in FIGS. 7D and 7E. As in the methods of FIGS. 8 and 9, a frame-containing structure 74 is prepared by combining a sintered PTFE tube and a structural frame. Independently, an electrospun PTFE sheet 84 is prepared and sintered; a combination PU/PTFE sheet 86 is prepared by electrospinning PU directly onto sheet 84. The combination sheet is wrapped around structure 74, with the PU layer laid directly against the outer surface (i.e., the structural frame) of structure 74. The entire device precursor is then subjected to pressure and heat simultaneously. The cross-section on the left (96) depicts the result of the above process wherein the combination sheet is wrapped once around the construct and the multi-component cross-section on the right (98) depicts the result of the above process wherein the combination sheet is wrapped twice around the construct.

As such, in one embodiment, the present disclosure provides a method for producing a composite prosthetic device comprising: applying a structural frame over a porous electrospun poly(tetrafluoroethylene) tubular structure; preparing a combination electrospun mat by electrospinning a different polymer onto a sintered poly(tetrafluoroethylene) mat; wrapping the combination electrospun mat around the construct (one or more times, with the different polymer mat surface in contact with the construct) to give a precursor; and applying heat and pressure to provide a composite prosthetic device.

Figure 11:
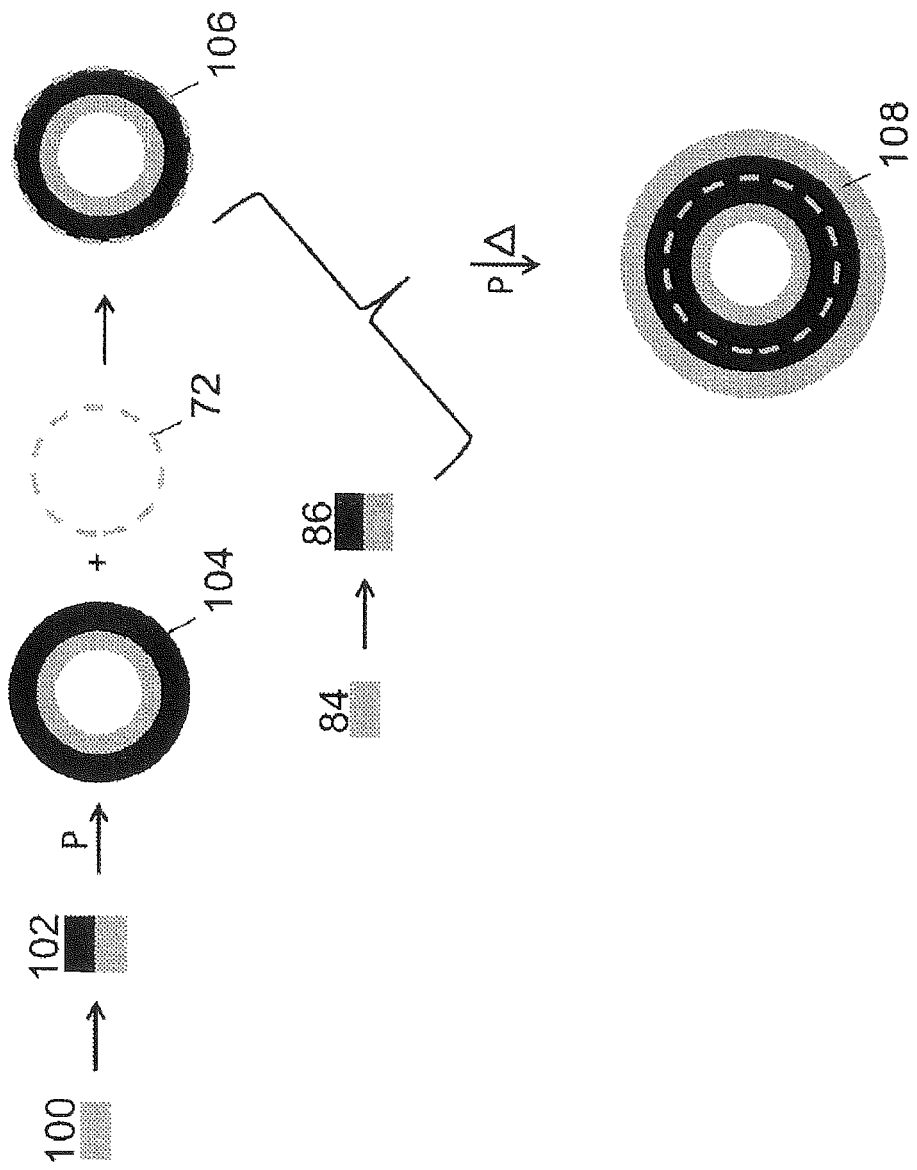
FIG. 11 is a schematic illustrating one exemplary process for the preparation of the exemplary composite device of FIG. 7F.

FIG. 11 illustrates an exemplary preparation of the composite device illustrated in FIG. 7F. An electrospun PTFE sheet 100 is prepared and sintered; a combination PU/PTFE sheet 102 is prepared by electrospinning PU directly onto sheet 100. Combination sheet 102 is wrapped to form a tubular structure (with the PTFE on the interior of the structure), which is then compressed to give structure 104. A structural frame 72 is applied around the compressed, tubular material to give frame-containing structure 106. Independently, an additional espun PTFE sheet 84 is prepared and sintered and a second combination PU/PTFE sheet 86 is prepared by electrospinning PU directly onto sheet 84. Sheet 86 is then wrapped around structure 106, with the PU layer laid directly against the outer surface (i.e., the structural frame) of structure 106. The resulting device precursor is subjected to pressure and heat to give multi-component prosthetic device 108.

As such, in one embodiment, the present disclosure provides a method for producing a composite prosthetic device comprising: preparing a combination electrospun mat by electrospinning a different polymer onto a sintered poly (tetrafluoroethylene) mat; forming the combination electrospun mat into a tubular structure having two or more alternating layers, wherein the poly(tetrafluoroethylene) surface of the mat is on the inner surface of the tubular structure and the different polymer surface of the mat is on the outer surface of the tubular structure; applying a structural frame over the outer surface of the tubular structure; preparing a second combination electrospun mat by electrospinning a different polymer onto a sintered poly(tetrafluoroethylene) mat; wrapping the combination electrospun mat around the construct (one or more times, with the different polymer mat surface in contact with the construct) to give a precursor; and applying heat and pressure to provide a composite prosthetic device.

EXAMPLES

Mono-Component Devices

Example 1: Espun PTFE/Espun PTFE/Espun PTFE

An espinning dispersion based on a mixture of 5.2% (PEO/PTFE) 300,000 amu polyethylene oxide and Daikin DX-9030, 60% PTFE dispersion in water is prepared, allowed to homogenize, and turned and filtered to achieve a smooth consistency. A 0.002" thick stainless steel foil sheet (15.5"×17.5") is mounted on a conductive fabric. The stainless foil is passed into the espinning chamber where PTFE fibers are to be deposited. The dispersion is espun using a total potential of 80 kV to facilitate formation of PTFE fibers, which collect in random formation on the stainless steel foil. The stainless steel foil containing the PTFE membrane is removed from the fabric and sintered at 385° C. until fully sintered (e.g., about 5 minutes).

The 0.0008" sintered espun PTFE sheet, removed from the stainless foil, is wrapped twice around a 0.50" exterior diameter (OD) stainless steel hypotube. The electrospinning process is repeated to give a second espun PTFE sheet. The espun PTFE sheet, a 0.0018" unsintered espun PTFE sheet, is removed from the stainless foil and wrapped twice around the sintered espun PTFE layer. The electrospinning process is repeated to give a third espun PTFE sheet, which is then sintered. The third espun PTFE sheet, a 0.0018" sintered espun PTFE sheet, is removed from the stainless foil after sintering and wrapped twice around the unsintered espun PTFE layer to create a tube assembly consisting of sintered espun PTFE/unsintered espun PTFE/sintered espun PTFE. The entire construction is then compressed together and heated/sintered at 385° C. for about 5-15 minutes (until fully bonded, as evidenced by lack of delamination), followed by water quenching as a means to cool down the sample. The composite device is then removed from the hypotube and tested for specified properties. The thickness of the construction was found to be approximately 0.005" and the effective pore size was found to be approximately 1.5 μm.

Example 2: Espun PTFE/Stent/Espun PTFE/Espun PTFE

Example 2 is made similarly to Example 1 with the addition of a wire stent frame as an additional layer of the composite. An espinning dispersion based on a mixture of 5.2% (PEO/PTFE) 300,000 amu polyethylene oxide and Daikin DX-9030, 60% PTFE dispersion in water is prepared, allowed to homogenize, and turned and filtered to achieve a smooth consistency. A 0.002" thick stainless steel foil sheet (15.5"×17.5") is mounted on a conductive fabric. The stainless foil is passed into the espinning chamber where PTFE fibers are to be deposited. The dispersion is espun using a total potential of 80 kV to facilitate formation of PTFE fibers, which collect in random formation on the stainless steel foil. The stainless steel foil containing the PTFE membrane is removed from the fabric and sintered at 385° C. for 5 minutes.

The 0.0008" sintered espun PTFE sheet, removed from the stainless foil, is wrapped twice around a 0.50" exterior diameter (OD) stainless steel hypotube. A metal stent frame is then applied over this 0.0008" sintered espun PTFE sheet. The electrospinning process is repeated to give a second espun PTFE sheet. The espun PTFE sheet, a 0.0018" unsintered espun PTFE sheet, is removed from the stainless foil and wrapped twice around the stent. The electrospinning process is repeated to give a third espun PTFE sheet, which is then sintered. The third espun PTFE sheet, a 0.0018" sintered espun PTFE sheet, is removed from the stainless foil after sintering and wrapped twice around the unsintered espun PTFE layer to create a tube assembly consisting of sintered espun PTFE/stent/unsintered espun PTFE/sintered espun PTFE. The entire construction is then compressed together and heated/sintered at 385° C. for 15 minutes, followed by water quenching as a means to cool down the sample. The composite device is then removed from the hypotube and tested for specified properties. The thickness of such a construction is found to approximately 0.005" and the effective pore size was found to be approximately 1.5 μm.

Multi-Component Devices

Example 3: Espun PTFE/Espun PVDF/Espun PTFE

An espinning dispersion based on a mixture of 5.2% (PEO/PTFE) 300,000 amu polyethylene oxide and Daikin DX-9030, 60% PTFE dispersion in water is prepared, allowed to homogenize, and turned and filtered to achieve a smooth consistency. A 0.002" thick stainless steel foil sheet (15.5"×17.5") is mounted on a conductive fabric roll with a payoff and take-up mounted above a spinning electrode. A total potential of 80 kV is employed to facilitate formation of PTFE fibers, which collect in random formation on the stainless steel foil. The stainless steel foil containing the PTFE membrane is removed from the fabric and sintered (if desired) at 385° C. for 5 minutes.

A 0.0015" thick stainless foil sheet 17"×18.5" is wrapped around a rotating drum. The drum assembly is placed into a rotating chuck such that it is positioned to allow espinning along the entire length of the turning drum assembly. An espinning solution based on a mixture of 25% Atofina Kynar 740 polyvinylidene fluoride (PVDF) and a 50/50 (by volume) mixture of acetone and dimethyl formamide is allowed to dissolve and mix using a heated stir plate set to 75° C. at 500 rpm for 1 hour. A voltage of 15.0 kV is employed to facilitate formation of PVDF fibers, which collect in random formation on the stainless foil sheet. The stainless soil sheet containing the PVDF mat is removed from the drum and dried for 1 hour at room temperature.

A 0.001" sintered espun PTFE sheet, removed from the stainless foil, is wrapped twice around a 0.50" exterior diameter (OD) stainless steel hypotube. The 0.001" espun PVDF sheet, removed from the stainless foil, is wrapped twice around the sintered espun PTFE layer. Finally, a 0.001" sintered espun PTFE sheet is wrapped twice around the espun PVDF layer to create a tube assembly consisting of sintered espun PTFE/espun PVDF/sintered espun PTFE. The entire construction is then compressed together prior to heating/sintering at 370° C. for 15 minutes followed by water quenching as a means to cool down the sample. The composite is then removed from the hypotube and tested for specified properties.

Example 4: Espun PTFE/Stent/Espun PVDF/Espun PTFE

Example 4 is made similarly to Example 3 with the addition of a wire stent frame as another support layer. An espinning dispersion based on a mixture of 5.2% (PEO/PTFE) 300,000 amu polyethylene oxide and Daikin DX-9030, 60% PTFE dispersion in water is prepared, allowed to homogenize, and turned and filtered to achieve a smooth consistency. A 0.002" thick stainless steel foil sheet (15.5"×17.5") is mounted on a conductive fabric roll with a payoff and take-up mounted above a spinning electrode. A total potential of 80 kV is employed to facilitate formation of PTFE fibers, which collect in random formation on the stainless steel foil. The stainless steel foil containing the PTFE membrane is removed from the fabric and sintered (if desired) at 385° C. for 5 minutes.

A 0.0015" thick stainless foil sheet 17"×18.5" is wrapped around a rotating drum. The drum assembly is placed into a rotating chuck such that it is positioned to allow espinning along the entire length of the turning drum assembly. An espinning solution based on a mixture of 25% Atofina Kynar 740 polyvinylidene fluoride (PVDF) and a 50/50 (by volume) mixture of acetone and dimethyl formamide is allowed to dissolve and mix using a heated stir plate set to 75° C. at 500 rpm for 1 hour. A voltage of 15.0 kV is employed to facilitate formation of PVDF fibers, which collect in random formation on the stainless foil sheet. The stainless soil sheet containing the PVDF mat is removed from the drum and dried for 1 hour at room temperature.

A 0.001" sintered espun PTFE sheet, removed from the stainless foil, is wrapped twice around a 0.50" exterior diameter (OD) stainless steel hypotube. A metal stent frame is then applied over this 0.001" sintered espun PTFE sheet. The 0.001" espun PVDF sheet, removed from the stainless foil, is wrapped twice around the metal stent. Finally, a 0.001" sintered espun PTFE sheet is wrapped twice around the espun PVDF layer to create a tube assembly consisting of sintered espun PTFE/stent/espun PVDF/sintered espun PTFE. The entire construction is then compressed together prior to heating/sintering at 370° C. for 15 minutes followed by water quenching as a means to cool down the sample. The composite is then removed from the hypotube and tested for specified properties.

Example 5: Espun PTFE/Stent/Espun PU Espun PTFE

A sintered espun PTFE sheet, prepared as described herein, is wrapped twice (could be more or less) around a metal hypotube (of any diameter) and sintered at 385° C. for 5 minutes (to prevent the PTFE layers from delaminating from one another) to form a sintered, espun PTFE tube (inner diameter surface) around the metal hypotube. This represents the ID surface of the device. A structural frame may or may not be applied over this sintered espun PTFE tube. The OD surface consists of a wrapped sheet, wrapped twice (as shown in FIG. 7E, but could be more or less) around the metal frame or sintered espun PTFE tube (if no metal frame is present). The wrapped sheet is a combination sheet that consists of PU espun (from solution) onto an espun PTFE sheet (prepared by spinning a dispersion), whereby the PU is in direct contact with the metal frame or sintered espun PTFE tube (if no metal frame is present). Thus, the OD surface is a sandwich of alternating layers of PU and PTFE (the number of layers dependent on the number of wraps). The espun PU can be either porous (more fiber-like) or non-porous (more film-like) depending on run conditions. The espun PU layer can also range in thickness, being as thin as 0.0001". Pressure and heat are then applied simultaneously to the device to bond all layers into one component. The thickness of the composite is based on the number of wraps and the thickness of the input material. The pore size is dependent on the processing of the input material as well as number of wraps.

Example 6: Espun PTFE/Stent/Espun PDMS/Espun PTFE

A sintered espun PTFE sheet, prepared as described herein, is wrapped twice (could be more or less) around a metal hypotube (of any diameter) and sintered at 385° C. for 5 minutes (to prevent the PTFE layers from delaminating from one another) to form a sintered, espun PTFE tube (inner diameter surface) around the metal hypotube. This represents the ID surface of the device. A structural frame may or may not be applied over this sintered espun PTFE tube. The OD surface consists of a sheet wrapped twice (could be more or less) around the metal frame or sintered espun PTFE tube (if no metal frame is present). The wrapped sheet consists of PDMS espun (from solution) onto an espun PTFE sheet (prepared by spinning a dispersion), whereby the PDMS is in direct contact with the metal frame or sintered espun PTFE tube (if no metal frame is present). Thus, the OD is a sandwich of alternating layers of PDMS and PTFE (the number of layers dependent on the number of wraps). The espun PDMS can be either porous (more fiber-like) or non-porous (more film-like) depending on run conditions. The espun PDMS layer can also range in thickness, being as thin as 0.0001". Pressure and heat are then applied simultaneously to the device to bond all layers into one component. The thickness of the composite is based on the number of wraps and the thickness of the input material. The pore size is dependent on the processing of the input material as well as number of wraps.

Many modifications and other embodiments of the invention will come to mind to one skilled in the art to which this disclosure pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for producing a composite prosthetic device comprising: combining, to give a composite prosthetic device precursor, (i) a structural frame, (ii) one or more first porous layers comprising electrospun poly(tetrafluoroethylene), (iii) one or more second porous layers comprising a first electrospun polymer, (iv) one or more third porous layers comprising electrospun poly(tetrafluoroethylene), and (v) one or more fourth porous layers comprising a second electrospun polymer, wherein at least one of the one or more second porous layers is disposed on at least part of a first side of the structural frame, and at least one of the one or more first porous layers is disposed on the at least one of the one or more second porous layers, and wherein at least one of the one or more fourth porous layers is disposed on at least part of a second side of the structural frame, and at least one of the one or more third porous layers is disposed on the at least one of the one or more fourth porous layers; and applying pressure, heat, or both pressure and heat to the composite prosthetic device precursor to provide the composite prosthetic device.

2. The method of claim 1, wherein the applying step comprises applying pressure, heat, or both pressure and heat for a time sufficient to result in penetration of the first elecrospun polymer of at least one of the one or more second porous layers into one or more pores of at least one of the one or more first porous layers.

3. The method of claim 1, wherein the first electrospun polymer is the same as the second electrospun polymer.

4. The method of claim 1, wherein the first side of the structural frame forms an inside diameter of the structural frame, and the second side of the structural frame forms an outside diameter of the structural frame.

5. The method of claim 1, wherein at least one of the one or more first porous layers and the one or more third porous layers comprise sintered electrospun poly(tetrafluoroethylene).

6. The method of claim 1, wherein the combining step comprises placing the structural frame around the one or more second porous layers.

7. The method of claim 6, wherein the structural frame is a stent.

8. The method of claim 1, wherein the structural frame comprises open spaces through which at least one of the first electrospun polymer and the second electrospun polymer penetrates.

9. The method of claim 1, wherein the combining comprises wrapping at least one of the one or more second porous layers around at least one of the one or more first porous layers.

10. The method of claim 1, wherein the combining comprises electrospinning at least one of the one or more second porous layers onto at least one of the one or more first porous layers.

11. The method of claim 1, wherein the first electrospun polymer comprises a solution-electrospun polymer.

12. The method of claim 1, wherein the first electrospun polymer comprises a thermoplastic polymer or a thermoset polymer.

13. The method of claim 1, wherein the first electrospun polymer layer comprises a polyurethane or a silicone.

14. The method of claim 1, wherein the first electrospun polymer is selected from the group consisting of polyether block amide, a polyamide, ultra-high molecular weight polyethylene, a polyester, fluorinated ethylene propylene, polyvinylidene fluoride, perfluoroalkoxy, tetrafluoroethylene/hexafluoropropylene/vinylidene fluoride copolymer, poly(ethylene-co-tetrafluoroethylene), ethylene chlorotrifluoroethylene, polychlorotrifluoroethylene, and copolymers, blends, and derivatives thereof.

15. The method of claim 1, wherein the first electrospun polymer comprises unsintered poly(tetrafluoroethylene) and wherein the applying step causes sintering of the composite prosthetic device.

16. The method of claim 1, wherein the applying step comprises applying pressure, heat, or both pressure and heat for a time sufficient to result in the penetration of the first electrospun polymer into pores of the one or more first porous layers.

17. The method of claim 1, wherein both pressure and heat are applied, sequentially or simultaneously.

18. The method of claim 1, wherein the pressure is between about 500 and about 1500 PSI and the temperature is between about 100.degree. C. and about 400.degree. C.

19. The method of claim 1, wherein the applying step is conducted in a pressure vessel.

* * * * *